US008108152B2

(12) United States Patent
Maranas et al.

(10) Patent No.: US 8,108,152 B2
(45) Date of Patent: *Jan. 31, 2012

(54) METHOD FOR REDESIGN OF MICROBIAL PRODUCTION SYSTEMS

(75) Inventors: Costas D. Maranas, State College, PA (US); Anthony P. Burgard, San Diego, CA (US); Priti Pharkya, San Diego, CA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/886,649

(22) Filed: Sep. 21, 2010

(65) Prior Publication Data

US 2011/0015867 A1    Jan. 20, 2011

Related U.S. Application Data

(60) Division of application No. 10/929,091, filed on Aug. 26, 2004, now Pat. No. 7,826,975, which is a continuation-in-part of application No. 10/616,659, filed on Jul. 9, 2003, now Pat. No. 8,027,821.

(60) Provisional application No. 60/395,763, filed on Jul. 10, 2002, provisional application No. 60/417,511, filed on Oct. 9, 2002, provisional application No. 60/444,933, filed on Feb. 3, 2003.

(51) Int. Cl.
*G06F 19/12* (2011.01)
*G06F 19/14* (2011.01)

(52) U.S. Cl. ........................................................ 702/19

(58) Field of Classification Search ........................ None
See application file for complete search history.

(56) References Cited

U.S. PATENT DOCUMENTS

| 4,520,103 | A | 5/1985 | Ensley, Jr. |
| 6,117,108 | A | 9/2000 | Woehr et al. |
| 7,127,379 | B2 | 10/2006 | Palsson et al. |
| 7,711,490 | B2 | 5/2010 | Maranas et al. |
| 2002/0012939 | A1 | 1/2002 | Palsson |
| 2003/0073092 | A1 | 4/2003 | Maranas et al. |
| 2004/0009466 | A1 | 1/2004 | Maranas et al. |
| 2005/0079482 | A1 | 4/2005 | Maranas et al. |

FOREIGN PATENT DOCUMENTS

| JP | 00/268018 | 3/1999 |
| WO | WO 98/18814 | 5/1998 |
| WO | WO 00/18906 | 4/2000 |
| WO | WO 00/42559 | 7/2000 |
| WO | WO 01/90346 A2 | 11/2001 |
| WO | WO 02/055995 A2 | 7/2002 |
| WO | PCT/US03/021598 | 7/2003 |

OTHER PUBLICATIONS

Anandalingam et al., "Hierarchical Optimization: An Introduction," Annals. Ops. Res. 34:1-11 (1992).

Arigoni et al., "A genome-based approach for the identification of essential bacterial genes," Nat. Biotechnol. 16(9):851-856 (1998).
Aristidou et al., "Modification of central metabolic pathway in *Escherichia coli* to reduce acetate accumulation by heterolgous expression of the *Bacillus subtilis* acetolactate synthase gene," Biotechnol. Bioeng. 44:944-951 (1994).
Aristidou et al., "Metabolic engineering applications to renewable resource utilization", Biochemical Engineering, pp. 187-198, 2000.
Arita, "The metabolic world of *Escherichia coli* is not small," Proc. Natl. Acad. Sci. U.S.A., 101(6):1543-1547 (2004).
Arita, "Metabolic construction using shortest paths," Simulation Practice and Theory, 8(1-2):109-125 (2000).
Badarinarayana et al., "Selection analyses of insertional mutants using subgenic-resolution arrays," Nat. Biotechnol. 19(11):1060-1065 (2001).
Bailey, "Complex biology with no parameters," Nat. Biotechnol. 19(6):503-504 (2001).
Bailey et al., "Combining evidence using p-values: application to sequence homology searches," Bioinformatics 14:48-54 (1998).
Bhaskar, et al., "Applications of Multiobjective Optimization in Chemical Engineering," Rev. Chem. Eng. 16(1):1-54 (2000).
Biebl, H. et al., "Microbial Production of 1,3-Propanediol", Appl Microbiol. Biotechnol (1999) 52:289-297 Mini-Review, 1999.
Blattner et al., "The complete genome sequence of *Escherichia coli* K-12," Science 277(5331):1453-1475 (1997).
Bogarad, Leonard, D. et al., "A Hierarchical Approach to Protein Molecular Evolution", Proc. Natl. Acad. Sci. USA, vol. 96, pp. 2591-2595, Mar. 1999.
Bond et al., Electricity Production by Geobacter Sulfurreducens Attached to Electrodes, Appl. Environ. Microbiol. 69(3):1548-1555 (2003).
Burgard, Anthony P., "Probing the Performance Limits of the *Escherichia coli* Metabolic Network Subject to Gene Additions or Deletions" 2001 John Wiley & Sons, Inc., Biotechnology & Bioengineering(Sep. 5, 2001), vol. 74, No. 5, p. 364-375.
Burgard, Anthony P. et al, ALCHE XP-002216514—[309D] — "Tightening Flux Balance Models Through Boolean Relations" 2001 American Institute of Chemical Engineers. Burgard et al., "Minimal Reaction Sets for *Escherichia coli* Metabolism under Different Growth Requirements and Uptake Environments," Biotechnol. Prog. 17(5):791-797 (2001).
Burgard et al., "Optknock: a bilevel programming framework for identifying gene knockout strategies for microbial strain optimization," Biotechnol. Bioeng. 84(6):647-657 (2003).
Burgard, Anthony P., "Optimization-Based Framework for Inferring and Testing Hypothesized Metabolic Objective Functions" 2003 Wiley Periodicals, Inc.
Cameron, D.C. et al., "Metabolic Engineering of Propanediol Pathways" Biotechnol. Prog. 1998, 14, 116-125, Published on Web Jan. 16, 1998.

(Continued)

*Primary Examiner* — Lori A Clow
(74) *Attorney, Agent, or Firm* — McKee, Voorhees & Sease, P.L.C.

(57) ABSTRACT

A computer-assisted method for identifying functionalities to add to an organism-specific metabolic network to enable a desired biotransformation in a host includes accessing reactions from a universal database to provide stoichiometric balance, identifying at least one stoichiometrically balanced pathway at least partially based on the reactions and a substrate to minimize a number of non-native functionalities in the production host, and incorporating the at least one stoichiometrically balanced pathway into the host to provide the desired biotransformation. A representation of the metabolic network as modified can be stored.

2 Claims, 6 Drawing Sheets

OTHER PUBLICATIONS

Castellanos et al., "A modular minimal cell model: purine and pyrimidine transport and metabolism," Proc. Natl. Acad. Sci. U.S.A., 101(17):6681-6686 (2004).

Causey et al., "Engineering *Escherichia coli* for efficient conversion of glucose to pyruvate," Proc. Natl. Acad. Sci. U. S.A., 101(8):2235-2240 (2004).

Causey et al., "Engineering the metabolism of *Escherichia coli* W3110 for the conversion of sugar to redox-neutral and oxidized products: Homoacetate production", PNAS 100(3):825-832 (2003).

Chen, Haoyuan et al., BioComputing XP-002250110 "Computer Program for Calculating the Melting Temperature of Degenerate Oligonucleotides Used in PCR or Hybridization" Bio Techniques 22:1158-1160 (Jun. 1997).

Chistoserdova et al., "Multiple formate dehydrogenase enzymes in the facultative methylotroph *Methylobacterium extorquens* AM1 are dispensable for growth on methanol," J. Bacteriol. 186:22-28 (2004).

Cho et al., "Ethical considerations in synthesizing a minimal genome," Science 286:2087-2090 (1999).

Chou et al., "Effect of modified glucose uptake using genetic engineering techniques on high-level recombinant protein production in *Escherichia colidense* cultures," Biotechnol. Bioeng. 44:952-960 (1994).

Compagno, Concetta et al. "Glycerol Production in a Triose Phosphate Isomerase Deficient Mutant of *Saccharomyces cerevisiae*" Biotechnol. Progm. 1996, 12, 591-595.

Covert, "Regulation of Gene Expression in Flux Balance Models of Metabolism," J. Theor. Biol. 213:73-88 (2001).

Covert et al., "Transcriptional regulation in constraints-based metabolic models of *Escherichia coli*," J. Biol. Chem. 277(31):28058-28064 (2002).

Datta et al., "Technological and economic potential of poly(lactic acid) and lactic acid derivatives," FEMS Microbiol. Rev. 16:221-231 (1995).

David et al., "Reconstruction of the central carbon metabolism of *Aspergillus niger*," Eur. J. Biochem. 270 (21):4243-4253 (2003).

Dedhia et al., "Overproduction of glycogen in *Escherichia coli* blocked in the acetate pathway improves cell growth," Biotechnol. Bioeng. 44:132-139 (1994).

Delgado et al., "Inverse Flux analysis for reduction of *Escherichia coli*," Biotechnol Prog. 13:361-367 (1997).

Delgado et al., "Identifying Rate-controlling Enzymes in Metabolic Pathways Without Kinetic Parameters," Biotechnol. Prog. 7:15-20 (1991).

Desai et al., "Stoichiometric modeling of Clostridium acetobutylicum fermentations with non-linear constraints," J. Biotechnol. 71(1-3):191-205 (1999).

Edwards et al., "How will bioinformatics influence metabolic engineering?" Biotechnol. Bioeng. 58(2-3):162-169 (1998).

Edwards et al., "Metabolic flux balance analysis and the in silico analysis of *Escherichia coli* K-12 gene deletions," BMC Bioinformatics 1(1):1-10 (2000).

Edwards, J. S. et al., "The *Escherichia coli* MG 1655 in silico metabolic genotype: Its definition, characteristics, and capabilities" PNAS May 9, 2000, vol. 97. No. 10.

Edwards, J. S. et al., "In silico predictions of *Escherichia coli* metabolic capabilities are consistent with experimental data" 2001 Nature Publishing Group; Nature Biotechnology, vol. 19, Feb. 2001.

Ellis et al., "The University of Minnesota Biocatalysis/Biodegradation Database: post-genomic data mining," Nucl. Acids Res. 31(1):262-265 (2003).

Finneran et al., "Multiple influences of nitrate on uranium solubility during bioremediation of uranium-contaminated subsurface sediments," Environ. Microbiol. 4(9):510-516 (2002).

Fisher, Marshall L., "The Lagrangian Relaxation Method for Solving Integer Programming Problems", Management Science 27(1):1-18 (1981).

Forster et al., "Genome-scale reconstruction of the *Saccharomyces cerevisiae* metabolic network," Genome Res. 13(2):244-253 (2003).

Forster, et al., "Large-Scale Evaluation of in Silico Gene Deletions in *Saccharomyces cerevisiae*", OMICS, A Journal of Integrative Biology 7(2):193-202 (2003).

Goebl et al., "Most of the yeast genomic sequences are not essential for cell growth and division," Cell 46(7):983-992 (1986).

Gupta, Shashi et al., "*Escherichia coli* Derivatives Lacking Both Alcohol Dehydrogenase and Phosphotransacetylase Grow Anaerobically by Lactate Fermentation" Journal of BActeriology, Jul. 1989, pp. 3650-3655.

Gupta et al., "A hierarchical lagrangean relaxation procedure for solving midterm planning problems," Ind. Eng. Chem. Res. 38:1937-1947 (1999).

Hartlep, M. et al., "Study of two-stage processes for the microbial production of 1,3-propanediol from glucose" Appl. Microbiol. Biotechnol. (2002) 60:60-66.

Hatzimanitatis, Vassily et al., "Analysis and Design of Metabolic Reaction Networks via Mixed-Integer Linear Optimization" AIChE Journal, May 1996, vol. 42, No. 5.

Hatzimanitatis et al. "Optimization of Regulatory Architectures in Metabolic Reaction Networks," Biotechnol. Bioeng. 52:485-500 (1996).

Hatzimanikatis et al., "Effects of Spatiotemporal Variations on Metabolic Control: Approximate Analysis Using (Log) Linear Kinetic Models," Biotechnol. Bioeng. 54(2):91-104 (1997).

Hatzimanikatis et al., "Application of mathematical tools for metabolic design of microbial ethanol production," Biotechnol. Bioeng. 58(2-3):154-161 (1998).

Hatzimanikatis, "A memorial review of Jay Bailey's contribution in prokaryotic metabolic engineering," Biotechnol. Bioeng. 79(5):504-508 (2002).

Heinrich et al., "A linear steady-state treatment of enzymatic chains. General properties, control and effector strength," Eur. J. Biochem. 42(1):89-95 (1974).

Henricksen et al., "Growth energetics and metabolic fluxes in continuous cultures of *Penicillium chrysogenum*," J. Biotechnol. 45:149-164 (1996).

Hugler, Michael et al. "Malonyl-Coenzyme a Reductase from Chloroflexus aurantiacus, a Key Enzyme of the 3-Hydroxypropionate Cycle for Autotrophic Co2 Fixation" Journal for Bacteriology, May 2002, pp. 2404-2410.

Hutchinson et al., "Global transposon mutagenesis and a minimal Mycoplasma genome," Science, 286 (5447):2165-2169 (1999).

Hyunen, "Constructing a minimal genome," Trends Genet. 16(3):116 (2000).

Ibarra, Rafael U. et al., "*Escherichia coli* K-12 undergoes adaptive evolution to achieve in silico predicted optimal growth" 2004 Nature Publishing, vol. 420, Nov. 14, 2002.

Itaya, "An estimation of minimal genome size required for life," FEBS Lett. 362(3)257-260 (1995).

Jorgensen et al., "Metabolic flux distributions in *Penicillium chrysogenum* during fed-batch cultivations," Biotechnol. Bioeng. 46(2):117-131 (1995).

Kanehisa et al., "The KEGG resource for deciphering the genome," Nucl. Acids Res. 32(Database issue):D277-80 (2004).

Kanehisa et al.," KEGG: kyoto encyclopedia of genes and genomes," Nucl. Acids Res. 28(1):27-30 (2000).

Karp et al., "The EcoCyc and MetaCyc databases," Nucl. Acids Res. 28(1):56-59 (2000).

Karp et al., "The EcoCyc Database," Nucl. Acids Res. 30(1):56-58 (2002).

Karp et al., "Eco Cyc: Encyclopedia of *Escherichia coli* genes and metabolism," Nuc. Acids Res. 27(1):55-58 (1999).

Kauffman, Kenneth J., et al., "Advances in flux balance analysis", Current Opinion in Biology, London, GB, Oct. 1, 2003, vol. 14, No. 5, pp. 491-496. XP004568103.

Keasling et al., "Engineering Polyphosphate Metabolism in *Escherichia coli*: Implications for Bioremediation of Inorganic Contaminants," Biotechnol. Bioeng. 58(2-3):321-239 (1998).

Klamt et al., "FluxAnalyzer: exploring structure, pathways, and flux distributions in metabolic networks on interactive flux maps," Bioinformatics. 19(2):261-269 (2003).

Kompala et al., "Cybernetic Modeling of Microbial Growth on Multiple Substrates," Biotechnol. Bioeng. 26 (11):1272-1281 (1984).

Korotkova et al., "Poly-beta-hydroxybutyrate biosynthesis in the facultative methylotroph methylobacterium extorquens AM1: identification and mutation of gap11, gap20, and phaR," J. Bacteriol. 184(22):6174-6181 (2002).

Krieger et al., "MetaCyc: a multiorganism database of metabolic pathways and enzymes," Nucl. Acids Res. 32 (Database issue), D438-D442 (2004).

Lee et al., "Recursive MILP model for finding all the alternate optima in LP models for metabolic networks," Comput. Chem. Eng. 24:711-716 (2000).

Li et al., "Synthesis of vanillin from glucose," J. Am. Chem. Soc. 120:10545-10546 (1998).

Liu et al., "Production of electricity during wastewater treatment using a single chamber microbial fuel cell," Environ. Sci. Technol. 38:2281-2285 (2004).

Majewski et al., "Simple constrained-optimization view of acetate overflow in *Escherichia coli*," Biotechnol. Bioeng. 35(7):732-738 (1990).

Maranas, "Tightening Flux Balance Models Through Boolean Relations, " American Institute of Chemical Enginners converence Proceedings, url:http://www.aiche.org/conferences/tech/program/paperdetail.asp, (retrieved Oct. 11, 2002).

Maranas, Costas D., et al., "Systems Engineering Challenges and Opportunities in Computational Biology", Proceedings Foundations of Computer-Aided Process Operations, Jan. 21, 2003, pp. 13-26, XP007909104.

Mavrovouniotis et al., "Computer-aided synthesis of biochemical pathways," Biotechnol. Bioeng. 36 (11):1119-1132 (1990).

McShan et al., "PathMiner: predicting metabolic pathways by heuristic search," Bioinformatics. 19(13):1692-1698 (2003).

Menendez, Castor et al. "Presence of Acetyl Coenzyme A (CoA) Carboxylase and Propionyl-CaA Carboxylase in Autotrophic Crenarchaeota and Indication for Operation of a 3-Hydroxypropionate Cycle in Autoptrophic Carbon Fixation", Journal of Bacteriology, Feb. 1999, p. 1088-1098.

Methé et al., "Genome of Geobacter sulfurreducens: metal reduction in subsurface environments," Science, 302 (5652):1967-9 (2003).

Misawa et al., "Production of beta-carotene in Zymomonas mobilis and Agrobacterium tumefaciens by introduction of the biosynthesis genes from Erwinia uredovora," Appl. Environ. Microbiol. 57(6):1847-1849 (1991).

Moore, Gregory L. et al., "Modeling DNA Mutation and Recombination for Directed Evolution Experiments" XP-002250109, J. Theor. Biol. (2000) 205, 483-503.

Moore, Gregory L. et al., "Predicting crossover generation in DNA shuffling" XP-002250111, PNAS Mar. 13, 2001, vol. 98, No. 6.

Mushegian et al., "A minimal gene set for cellular life derived by comparison of complete bacterial genomes," Proc. Natl. Acad. Sci. U.S.A., 93(19):10268-10273 (1996).

Nakamura et al., "Metabolic engineering for the microbial production of 1,3-propanediol," Curr. Opin. Biotechnol. 14 (5):454-459 (2003).

Andi et al., "Microbial production of hydrogen: an overview," Crit. Rev. Microbiol. 24(1):61-84 (1998).

Oh et al., "Gene expression profiling by DNA microarrays and metabolic fluxes in *Escherichia coli*," Biotechnol. Prog. 16(2):278-286 (2000).

Overbeek et al., "WIT: integrated system for high-throughput genome sequence analysis and metabolic reconstruction," Nucl. Acids. Res. 28(1):123-125 (2000).

Palsson, Bernhard, "The challenges of in silico biology", Nature Biotechnology 18:1147-1150 (2000).

Papin et al., "Metabolic pathways in the post-genome era," Trends. Biochem. Sci. 28(5):250-258 (2003).

Papin et al., "The Genome-Scale Metabolic Extreme Pathway Structure in Haemophilus influenzae Shows Significant Network Redundancy", J. theor. Biol 215:67-82 (2002).

Papoutsakis, "Equations and calculations for fermentations of butyric acid bacteria," Biotechnol. Bioeng. 26 (2):174-187 (1984).

Papoutsakis et al., "Equations and Calculations of Product Yields and Preferred Pathways for Butanediol and Mixed-Acid Fermentations", Biotechnology and Bioengineering 17:50-66 (1985).

Pennisi, "Laboratory Workhorse Decoded," Science 277:1432-1434 (1997).

Petkov et al., "Quantitative Assessment of Uncertainty in the Optimization of Metabolic Pathways", Biotechnology and Bioengineering 56(2):145-161 (1997).

Pharkya, Priti, et al., "OptStrain: A computational framework for redesign of microbial production systems", Genome Res. 2004 14: 2367-2376. XP007909103.

Pramanik, J. et al., "Stoichiometric Model of *Escherichia coli* Metabolism: Incorporation of Growth-Rate Dependent Biomass Composition and Mechanistic Energy Requirements" 1997 John Wiley & Sons, Inc.

Yang, Yea-Tyng et al. "Genetic and metabolic engineering" EJB Electronic Journal of Biotechnology ISSN: 0717-3458 vol. 1, No. 3, Jan. 4, 2002.

Zeikus, J.G. et al. "Biotechnology of succinic acid production and markets for derived industrial products" Appl. Microbiol. Biotechnol. (1999) 51:545-552.

Zeng, An-Ping et al. "Bulk Chemical from Biotechnology: The case of 1,3-Propanediol Production and the New Trends" Advances in Biochemical Engineering/Biotechnology, vol. 74, 2002.

Zhu, Marie M. et al. "Improving 1,3-Propanediol Production from Blycerol in a Metabolically Engineered *Escherichia coli* by reducing Accumulation of sn-Glycerol-3-phosphate" Biotechnol. Prog. 2002, 18, 694-699.

"Appendix 1:Flux Balance Analysis Primer" www.che.udel.edu/edwardsgroup/LAB/NBT_ExpPhPP/FBAprimer/FBAC, Jan. 4, 2002.

Price et al, "Genome-scale Microbial in Silico Models: The Constraints-Based Approach," Trends Biotechnol. 21(4):162-169 (2003).

Quackenbush et al., The power of public access: the human genome project and the scientific porcess, Nat. Genet. 29:(1):4-6 (2001).

Ramakrishna et al., "Cybernetic Modeling of Growth in Mixed, Substitutable Substrate Environments: Preferential and Simultaneous Utilization," Biotechnol Bioeng. 52(1):141-151 (1996).

Ramakrishna et al., "Flux-balance analysis of mitochondrial energy metabolism: consequences of systemic stoichiometric constraints," Am J Physiol Regul Integr Comp Physiol, 280(3):R695-704 (2001).

Reed et al., "An expanded genome-scale model of *Escherichia coli* K-12 (iJR904 GSM/GPR)," Genome Biol. 4(9):R54 (2003).

Richmond et al., "Genome-wide expression profiling in *Escherichia coli* K-12," Nucl. Acids. Res. 27(19):3821-3835 (1999).

Santalucia, Jr., John, "A unified view of polymer, dumbbell, and oligonucleotide DNA nearest-neighbor thermodynamics" Proc. Natl. Acd. Sci. USA, vol. 95, pp. 1460-1465, Feb. 1998.

Savageau, Michael A., "Biochemical Systems Analysis, Part I. Some Mathematical Properties of the Rate Law for the Component Enzymatic Reactions", J. Theoret. Biol. 25:365-369 (1969).

Savageau, "Biochemical systems analysis, II: the steady stte solutions for an n-pool system using a power-law approximation," J. Theor. Biol. 25:370-379 (1969).

Schilling et al., "Toward metabolic phenomics: analysis of genomic data using flux balances," Biotechnol Prog, 15:288-295 (1999).

Schilling et al., "Assessment of the metabolic capabilities of *Haemophilus influenzae* Rd through a genome-scale pathway analysis," J. Theor. Biol. 203(3):249-83 (2000).

Schilling et al., "Combining pathway analysis with flux balance analysis for the comprehensive study of metabolic systems," Biotechnol. Bioeng. 71(4):286-306 (2000).

Schilling, Christophe H. et al., "Combining Pathway Analysis with Flux Balance Analysis for the Comprehensive Study of Metabolic Systems" XP-002216515; 2001 John Wiley & Sons, Inc.

Schilling et al., "Genome-scale metabolic model of Helicobacter pylon 26695," J. Bacteriol. 184(16):4582-4593 (2002).

Schuster et al., "Detection of elementary flux modes in biochemical networks: a promising tool for pathway analysis and metabolic engineering," Tibech. 17:53-60 (1999).

Segre, Daniel et al., "Analysis of optimally in nature and perturbed metabolic networks" PNAS Nov. 12, 2002, vol. 99, No. 23.

Segre et al., "From annotated genomes to metabolic flux models and kinetic parameter fitting," Omics 7(3):301-316 (2003).

Selkov et al., "MPW: the Metabolic Pathways Database," Nucl Acids Res, 26(1):43-45 (1998).

Snell et al., "Genome evolution. Gene fusion versus gene fission," Trends Genet. 16(1):9-11 (2000).

Supplemental European Search Report EP03792962 dated Apr. 11, 2007.

Supplemental European Search Report, The Penn State Research Foundation, EP 04 78 2168, dated Jul. 8, 2009, 2 pages.

Stols, Lucy "Production of Succinic Acid through Overexpression of NAD+-Dependent Malic Enzyme in an *Escherichia coli* Mutant", Applied and Environmental Microbiology, Jul. 1997, p. 2695-2701.

Sun, Fengzhu "Modeling DNA Shuffling" XP-002145606; GO6G19/00A2; p. 251-257, Dept. of Genetics RECOMB 1998.

TIGR-Web site. TIGR microbial database http://www.cmr.jcvi.org (2000) Not Available.

TIGR, Genomes, Medicine, and the Environment Conference, Oct. 16-18, 2006, http://web.archive.org/web/20060712190022/http://www.tigr.org (Sep. 18, 2009).

Tomita et al., "E-CELL: software environment for whole-cell simulation," Bioinformatics, 15(1):72-84 (1999).

Torres et al., "Optimization of nonlinear biotechnological processes with linear programming: application to citric acid production by *Aspergillus niger*," Biotechnol. Bioeng. 49:247-258 (1996).

Torres et al., "An Indirect Optimization Method for Biochemical Systems: Description of Method and Application to the Maximization of the Rate of Ethanol, Glycerol, and Carbohydrate Production in *Saccharomyces cerevisiae*", Biotechnology and Engineering 55(5):758-772 (1997).

Valdes et al., "Metabolic reconstruction of sulfur assimilation in the extremophile *Acidithiobacillus ferrooxidans* based on genome analysis," BMC Genomics 4:51 (2003).

Vallino et al., "Metabolic flux distributions in *Corynebacterium glutamicum* during growth and lysine overproduction," Biotechnol. Bioeng. 41:633-646 (1993).

Van Dien et al., "Optimization of Polyphosphate Degradation and Phosphate Secretion Using Hybrid Metabolic Pathways and Engineered Host Strains", Biotechnology and Engineering 59(6):754-761, 1998.

Van Dien et al., "Stoichiometric model for evaluating the metabolic capabilities of the facultative methylotroph *Methylobacterium extorquens* AM1, with application to reconstruction of C(3) and C(4) metabolism," Biotechnol. Bioeng. 78(3):296-312 (2002).

Van Dien et al., "Quantification of central metabolic fluxes in the facultative methylotroph methylobacterium extorquens AM1 using 13C-label tracing and mass spectrometry," Biotechnol. Bioeng. 84(1):45-55 (2003).

Varma et al., "Biochemical production capabilities of *Escherichia coli*," Biotechnol. Bioeng. 42(1)59-73 (1993).

Varma et al., "Metabolic Capabilities of *Escherichia coli*: I. Synthesis of Biosynthetic Precursors and Cofactors", J. theor. Biol. 165:477-502 (1993).

Varma et al., "Metabolic Capabilities of *Escherichia coli*: II. Optimal Growth Patterns," J. Theor. Biol. 165:503-522 (1993).

Varma et al., "Metabolic Flux Balancing: Basic Concepts, Scientific and Practical Use," Biotechnol. 12:994-998 (1993).

Varma et al., "Stoichiometric Interpretation of *Escherichia coli* Glucose Catabolism Under Various Oxygenation Rates.," Appl. Environ. Microbiol. 59(8):2465-2473 (1993).

Varma et al., "Stoichiometric flux balance models quantitatively predict growth and metabolic by-product secretion in wild-type *Escherichia coli* W3110," Appl. Environ. Microbiol. 60(10):3724-3731 (Oct. 1994).

Varner et al., "Metabolic engineering from a cybernetic perspective. 1. Theoretical preliminaries," Biotechnol. Prog. 15(3):407-425 (1999).

Varner et al., "Mathematical Models of Metabolic Pathways," Curr. Opin. Biotechnol. 10(2):146-150 (Apr. 1999).

Voit, "Optimization in Integrated Biochemical Systems," Biotechnol Bioeng, 40(5):572-582 (1992).

Wang et al., "Cadmium removal by a new strain *Pseudomonas aeruginosa* in aerobic culture," App. Environ. Microbiol. 63:4075-4078 (1997).

Winter et al., "Efficient degradation of trichloroethylene by a recombinant *Escherichia coli*," Bio/Technol. 7:282-285 (1989).

Xie et al., "Stoichiometric analysis of animal cell growth and its application in medium design," Biotechnol. Bioeng. 43 (11):1164-1174 (1994).

Xie et al., "High cell density and high monoclonal antibody production through medium design and rational control in a bioreactor," Biotechnol. Bioeng. 51(6):725-729 (1996).

Xie et al., "Applications of improved stochiometric model in medium design and fed-batch cultivation of animal cells in bioreactor," Cytotechnology 15(1-3):17-29 (1994).

Xie et al., "Energy metabolism and ATP balance in animal cell cultivation using a stoichiometrically based reaction network," Biotechnol. Bioeng. 52(5):591-601 (1996).

Xie et al., "Material Balance Studies on Animal Cell Metabolism Using Stoichiometrically Based Reaction Network," Biotechnol. Bioeng. 52:579-590 (1996).

Xie et al., "Integrated approaches to the design of media and feeding strategies for fed-batch cultures of animal cells," Trends Biotechnol. 15(3):109-113 (1997).

*Step 1:*

*Step 2:*

*Step 3:*

*Step 4:* maximize biochemical production (OptKnock)
(by reaction eliminations)

subject to | maximize biomass formation (Primal)
(over fluxes)
subject to
• fixed substrate uptake
• network stoichiometry
• blocked reactions identified by outer problem
• bounds on $O_2$, $CO_2$ and $NH_3$ transport rates Number of knockouts ≤ limit

Figure 6

METHOD FOR REDESIGN OF MICROBIAL PRODUCTION SYSTEMS

CROSS-REFERENCE TO RELATED APPLICATIONS

This application is a divisional application of U.S. Ser. No. 10/929,091 filed Aug. 26, 2004, which is a continuation-in-part of U.S. patent application Ser. No. 10/616,659, filed Jul. 9, 2003 which is a conversion of: U.S. Patent Application Ser. No. 60/395,763, filed Jul. 10, 2002; U.S. Patent Application Ser. No. 60/417,511, filed Oct. 9, 2002; and U.S. Patent Application Ser. No. 60/444,933, filed Feb. 3, 2003, all of which are herein incorporated by reference in their entireties.

GRANT REFERENCE

This invention was made with government support under Grant No. DE-FG03-01ER25499, awarded by the Department of Energy and Grant No. BES0120277, awarded by the National Science Foundation. The Government has certain rights in the invention.

BACKGROUND OF THE INVENTION

The present invention relates to a computational framework that guides pathway modifications, through reaction additions and deletions.

The generation of bioconversion pathways has attracted significant interest in recent years. The first systematic effort towards this end was made by Seressiotis and Bailey (Seressiotis & Bailey, 1988), who utilized the concepts of Artificial Intelligence in developing their software. This was followed by a case study on the production of lysine from glucose and ammonia performed by Mavrovouniotis et al. (Mavrovouniotis et al., 1990) utilizing an algorithm based on satisfying the stoichiometric constraints on reactions and metabolites in an iterative fashion. More recently, elegant graph theoretic concepts (e.g., P-graphs (Fan et al., 2002) and k-shortest paths algorithm (Eppstein, 1994)) were pioneered to identify novel biotransformation pathways based on the tracing of atoms (Arita, 2000; Arita, 2004), enzyme function rules and thermodynamic feasibility constraints (Hatzimanikatis et al., 2003). Most of these approaches have been demonstrated by applying them on a relatively small database of reactions. Their performance on genome-scale databases of metabolic reactions, such as the KEGG database which consists of approximately 5000 reactions (Kanehisa et al., 2002), will dramatically suffer.

Very recently, a heuristic approach based on determining the minimum pathway cost (based on any biochemical property) was proposed (McShan et al., 2003). This approach is quite successful in delineating the pathways for conversion of one metabolite into another. However, like all other approaches discussed earlier, it fails to predict the yield of the product obtained by employing a specific pathway. Furthermore, these approaches mostly identify linear biotransformation pathways without ensuring the balanceability of all metabolites, especially the cofactors.

Therefore it is a primary object, feature, or advantage of the present invention to provide an optimization-based procedure which addresses the complexity associated with genome-scale networks.

It is a further object, feature, or advantage of the present invention to provide a method for constructing stoichiometrically-balanced bioconversion pathways, both branched and linear, that are efficient in terms of yield and the number of non-native reactions required in a host for product formation.

Another object, feature, or advantage of the present invention is to provide a method that enables the evaluation of multiple substrate choices.

Yet another object, feature, or advantage of the present invention is to provide a method for computationally suggesting the manner in which to achieve bioengineering objectives, including increased production objectives.

A further object, feature or advantage of the present invention is to determine candidates for gene deletion or addition through use of a model of a network of bioconversion pathways.

Yet another object, feature or advantage of the present invention is to provide an optimized method for computationally achieving a bioengineering objective that is flexible and robust.

A still further object, feature, or advantage of the present invention is to provide a method for computationally achieving a bioengineering objective that can take into account not only central metabolic pathways, but also other pathways such as amino acid biosynthetic and degradation pathways.

Yet another object, feature, or advantage of the present invention is to provide a method for computationally achieving a bioengineering objective that that can take into account transport rates, secretion pathways or other characteristics as optimization variables.

One or more of these and/or other objects, features and advantages of the present invention will become apparent after review of the following detailed description of the disclosed embodiments and the appended claims.

BRIEF SUMMARY OF THE INVENTION

The present invention provides hierarchical computational framework, which is referred to as "OptStrain" and is aimed at guiding pathways modifications, through reaction additions and deletions, of microbial networks for the overproduction of targeted compounds. These compounds may range from electrons or hydrogen in bio-fuel cell and environmental applications to complex drug precursor molecules. A comprehensive database of biotransformations, referred to as the Universal database (with over 5,000 reactions), is compiled and regularly updated by downloading and curating reactions from multiple biopathway database sources. Combinatorial optimization is then employed to elucidate the set(s) of non-native functionalities, extracted from this Universal database, to add to the examined production host for enabling the desired product formation. Subsequently, competing functionalities that divert flux away from the targeted product are identified and removed to ensure higher product yields coupled with growth. The present invention represents a significant advancement over earlier efforts by establishing an integrated computational framework capable of constructing stoichiometrically balanced pathways, imposing maximum product yield requirements, pinpointing the optimal substrate(s), and evaluating different microbial hosts.

The range and utility of OptStrain is demonstrated by addressing two very different product molecules. The hydrogen case study pinpoints reaction elimination strategies for improving hydrogen yields using two different substrates for three separate production hosts. In contrast, the vanillin study primarily showcases which non-native pathways need to be added into *Escherichia coli*. In summary, OptStrain provides a useful tool to aid microbial strain design and, more importantly, it establishes an integrated framework to accommodate future modeling developments.

The OptStrain process incorporates the OptKnock process which has been previously described in U.S. patent application Ser. No. 10/616,659, filed July 9, U.S. Patent Application Ser. No. 60/395,763, filed Jul. 10, 2002, U.S. patent application Ser. No. 60/417,511, filed Oct. 9, 2002, and U.S. Patent Application Ser. No. 60/444,933, filed Feb. 3, 2003, all of which have been previously incorporated by reference in their entirety. The OptKnock process provides for the systematic development of engineered microbial strains for optimizing the production of chemical or biochemicals which is an overarching challenge in biotechnology. The advent of genome-scale models of metabolism has laid the foundation for the development of computational procedures for suggesting genetic manipulations that lead to overproduction. This is accomplished by ensuring that a drain towards growth resources (i.e., carbon, redox potential, and energy) is accompanied, due to stoichiometry, by the production of a desired production. Specifically, the computation framework identifies multiple gene deletion combinations that maximally couple a postulated cellular objective (e.g., biomass formation) with externally imposed chemical production targets. This nested structure gives rise to a bilevel optimization problem which is solved based on a transformation inspired by duality theory. This procedure of this framework, by coupling biomass formation with chemical production, suggest a growth selection/adaption system for indirectly evolving overproducing mutants.

OptKnock can also incorporate strategies that not only include central metabolic network genes, but also the amino acid biosynthetic and degradation pathways. In addition to gene deletions, the transport rates of carbon dioxide, ammonia and oxygen as well as the secretion pathways for key metabolites can be introduced as optimization variables in the framework. Thus, the present invention is both robust and flexible in order to address the complexity associated with genome-scale networks.

BRIEF DESCRIPTION OF THE DRAWINGS

FIG. 6 depicts the bilevel optimization structure of Optknock. The inner problem performs the flux allocation based on the optimization of a particular cellular objective (e.g., maximization of biomass yield, MOMA). The outer problem then maximizes the bioengineering objective (e.g., chemical production) by restricting access to key reactions available to the optimization of the inner problem.

DETAILED DESCRIPTION OF THE PREFERRED EMBODIMENT

Figure 1:
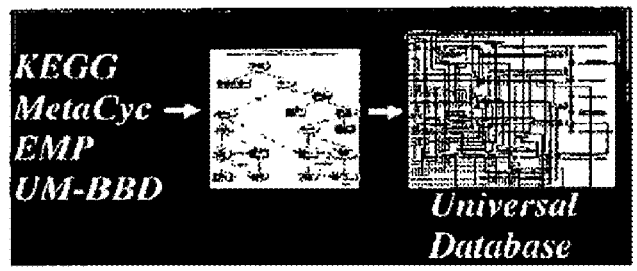
FIG. 1 is a pictorial representation of the OptStrain procedure. Step 1 involves the curation of database(s) of reactions to compile the Universal database which comprises of only elementally balanced reactions. Step 2 identifies a path enabling the desired biotransformation from a substrate (e.g., glucose, methanol, xylose) to product (e.g., hydrogen, vanillin) without any consideration for the origin of reactions. Note that the both, native reactions of the host and non-native reactions, are present. Step 3 minimizes the reliance on non-native reactions while Step 4 incorporates the non-native functionalities into the microbial host's stoichiometric model and applies the OptKnock procedure to identify and eliminate competing reactions with the targeted product. The (X)'s pinpoint the deleted reactions.
Figure 1:
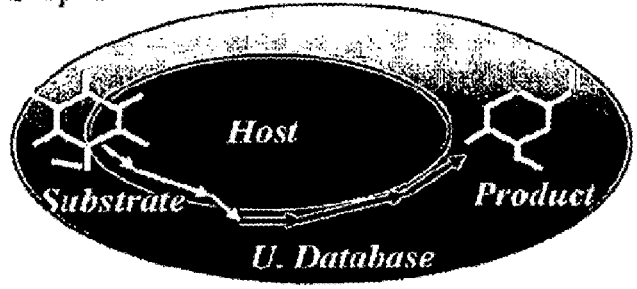
Figure 1:
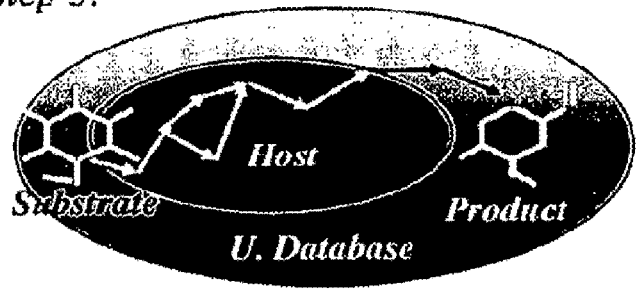
Figure 1:
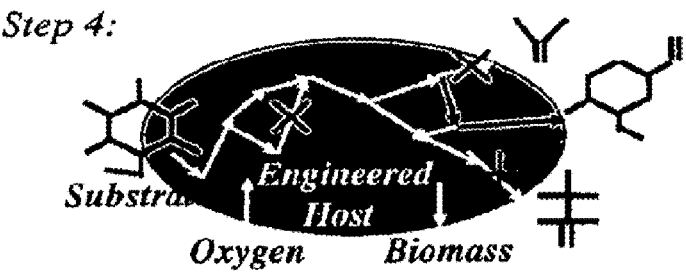

The present invention provides for methods and systems for guiding pathway modifications, through reaction additions and deletions. Preferably the methods are computer implemented or computer assisted or otherwise automated. The term "computer" as used herein should be construed broadly to include, but not to be limited to, any number of electronic devices suitable for practicing the methodology described herein. It is further to be understood that because the invention relates to computer-assisted modeling that the scope of the invention is broader than the specific embodiments provided herein and that one skilled in the art would understand how to apply the present invention in different environments and contexts to address different problems in part due to the predictability associated with computer implementations.

1. OptStrain

A fundamental goal in systems biology is to elucidate the complete "palette" of biotransformations accessible to nature in living systems. This goal parallels the continuing quest in biotechnology to construct microbial strains capable of accomplishing an ever-expanding array of desired biotransformations. These biotransformations are aimed at products that range from simple precursor chemicals (Nakamura & Whited, 2003; Causey et al., 2004) or complex molecules such as carotenoids (Misawa et al., 1991), to electrons in bio fuel cells (Liu et al., 2004) or batteries (Bond et al., 2002; Bond et al., 2003) to even microbes capable of precipitating heavy metal complexes in bioremediation applications (Methe et al., 2003; Lovley, 2003; Finneran et al., 2002). Recent developments in molecular biology and recombinant DNA technology have ushered a new era in the ability to shape the gene content and expression levels for microbial production strains in a direct and targeted fashion (Bailey, 1991; Stephanopoulos & Sinskey, 1993). The astounding range and diversity of these newly acquired capabilities and the scope of biotechnological applications imply that now more than ever we need modeling and computational aids to a priori identify the optimal sets of genetic modifications for strain optimization projects.

The recent availability of genome-scale models of microbial organisms has provided the pathway reconstructions necessary for developing computational methods aimed at identifying strain engineering strategies (Bailey, 2001). These models, already available for *H. pylori* (Schilling et al., 2002), *E. coli* (Reed et al., 2003; Edwards & Palsson, 2000), *S. cerevisiae* (Forster et al., 2003) and other microorganisms (David et al., 2003; Van Dien & Lindstrom, 2002; Valdes et al., 2003) provide successively refined abstractions of the microbial metabolic capabilities. An automated process to expedite the construction of stoichiometric models from annotated genomes (Segre et al., 2003) promises to further accelerate the metabolic reconstructions of several microbial organisms. At the same time, individual reactions are deposited in databases such as KEGG, EMP, MetaCyc, UM-BBD, and many more (Overbeek et al., 2000; Selkov et al., 1998; Kanehisa et al., 2004; Krieger et al., 2004; Ellis et al., 2003; Karp et al., 2002), forming encompassing and growing collections of the biotransformations for which we have direct or indirect evidence of existence in different species. Already many thousands of such reactions have been deposited; however, unlike organism specific metabolic reconstructions (Schilling et al., 2002; Reed et al., 2003; Edwards & Palsson, 2000; Forster et al., 2003), these compilations include reactions from not a single but many different species in a largely uncurated fashion. This means that currently there exists an ever-expanding collection of microbial models and at the same time ever more encompassing compilations of non-native functionalities. This newly acquired plethora of data has brought to the forefront a number of computational and modeling challenges which form the scope of this article. Specifically, how can we systematically select from the thousands of functionalities catalogued in various biological databases, the appropriate set of pathways/genes to recombine into existing production systems such as *E. coli* so as to endow them with the desired new functionalities? Subsequently, how can we identify which competing functionalities to eliminate to ensure high product yield as well as viability?

Existing strategies and methods for accomplishing this goal include database queries to explore all feasible bioconversion routes from a substrate to a target compound from a given list of biochemical transformations (Seressiotis & Bailey, 1988; Mavrovouniotis et al., 1990). More recently, elegant graph theoretic concepts (e.g., P-graphs (Fan et al., 2002) and k-shortest paths algorithm (Eppstein, 1994)) were pioneered to identify novel biotransformation pathways based on the tracing of atoms (Arita, 2000; Arita 2004), enzyme function rules and thermodynamic feasibility constraints (Hatzimanikatis et al., 2003). Also an interesting heuristic search approach that uses the enzymatic biochemical reactions found in the KEGG database (Kanehisa et al., 2004) to construct a connected graph linking the substrate and product metabolites was recently proposed (McShan et al., 2003). Most of these approaches, however, generate linear paths that link substrates to final products without ensuring that the rest of the metabolic network is balanced and that metabolic imperatives on cofactor usage/generation and energy balances are met.

The present invention provides a hierarchical optimization-based framework, OptStrain to identify stoichiometrically-balanced pathways to be generated upon recombination of non-native functionalities into a host organism to confer the desired phenotype. Candidate metabolic pathways are identified from an ever-expanding array of thousands (currently 5,734) of reactions pooled together from different stoichiometric models and publicly available databases such as KEGG (Kanehisa et al., 2004). Note that the identified pathways satisfy maximum yield considerations while the choice of substrates can be treated as optimization variables. Important information pertaining to the cofactor/energy requirements associated with each pathway is deduced enabling the comparison of candidate pathways with respect to the aforementioned criteria. Production host selection is examined by successively minimizing the reliance on heterologous genes while satisfying the performance targets identified above. A gene set that encodes for all the enzymes needed to catalyze the identified non-native functionalities can then be constructed accounting for isozymes and multi-subunit enzymes. Subsequently, gene deletions are identified (Burgard et al., 2003; Pharkya et al., 2003) in the augmented host networks to improve product yields by removing competing functionalities which decouple biochemical production and growth objectives. The breadth and scope of OptStrain is demonstrated by addressing in detail two different product molecules (i.e., hydrogen and vanillin) which lie at the two extremes in terms of product molecule size. Briefly, computational results in some cases match existing strain designs and production practices whereas in others pinpoint novel engineering strategies.

1.1 Materials and Methods

The first challenge addressed is to develop a systematic computational framework to identify which functionalities to add to the organism-specific metabolic network (e.g., *E. coli* (Reed et al., 2003; Edwards & Palsson, 2000), *S. cerevisiae* (Forster et al., 2003), *C. acetobutylicum* (Desai et al., 1999; Papoutsakis, 1984), etc.) to enable the desired biotransformation. The present inventors have already contributed towards this objective at a much smaller scale (Burgard & Maranas, 2001). Due to the extremely large size of the compiled database and the presence of multiple and sometimes conflicting objectives that need to be simultaneously satisfied, we developed the OptStrain procedure illustrated in FIG. 1. Each step introduces different computational challenges arising from the specific structure and size of the optimization problems that need to be solved.

Step 1. Automated downloading and curation of the reactions in our Universal database to ensure stoichiometric balance;

Step 2. Calculation of the maximum theoretical yield of the product given a substrate choice without restrictions on the reaction origin (i.e., native or non-native);

Step 3. Identification of a stoichiometrically-balanced pathway(s) that minimizes the number of non-native functionalities in the examined production host given the maximum theoretical yield and the optimum substrate(s) found in Step 2. Alternative pathways that meet both criteria of maximum yield and minimum number of heterologous genes are generated along with comparisons between different host choices. Information pertaining to the cofactor/energy usage associated with each pathway is also derived at this stage. Finally, one or multiple gene sets can be derived at this stage that ensure the presence of the targeted biotransformations by encoding for the appropriate enzymes;

Step 4. Incorporation of the identified non-native biotransformations into the stoichiometric models, if available, of the examined microbial production hosts. The OptKnock framework is next applied (Burgard et al., 2003; Pharkya et al., 2003) on these augmented models to suggest gene deletions that ensure the production of the desired product becomes an obligatory byproduct of growth by "shaping" the connectivity of the metabolic network. The OptKnock framework is further described herein.

Curation of the database. The first step of the OptStrain procedure begins with the downloading and curation of reactions acquired from various sources in our Universal database. Specifically, given the fact that new reactions are incorporated in the KEGG database on a monthly basis, we have developed customized scripts using Perl (Brown, 1999) to automatically download all reactions in the database on a regular basis. A different script is then used to parse the number of atoms of each element in every compound. The number of atoms of each type among the reactants and products of all reactions are calculated and reactions which are elementally unbalanced are excluded from consideration. In addition, compounds with an unspecified number of repeat units, (e.g., trans-2-Enoyl-CoA represented by $C_{25}H_{39}N_7O_{17}P_3S(CH_2)_n$) or unspecified alkyl groups R in their chemical formulae are removed from the downloaded sets. This step enables the automated downloading of functionalities present in genomic databases and the subsequent verification of their elemental balanceabilities forming large-scale sets of functionalities to be used as recombination targets.

The present invention, contemplates that any number of particular methods can be used to automate the duration and/or curation of reactions. These automated functions can be performed in any number of ways depending upon the resources available, the type of access to the resources, and other factors related to the specific environment or context in which the present invention is implemented.

Determination of the maximum yield. Once the reaction sets are determined, the second step is geared towards determining the maximum theoretical yield of the target product from a range of substrate choices, without restrictions on the number or origin of the reactions used. The maximum theoretical product yield is obtained for a unit uptake rate of substrate by maximizing the sum of all reaction fluxes producing minus those consuming the target metabolite, weighted by the stoichiometric coefficient of the target metabolite in these reactions. The maximization of this yield subject to stoichiometric constraints and transport conditions yields a Linear Programming (LP) problem (see Supporting Information for mathematical formulation), often encountered in Flux Balance Analysis frameworks (Varma & Palsson, 1994). Given the computational tractability of LP problems, even for many thousands for reactions, a large number of different substrate choices can thoroughly be explored here.

Although, in this specific embodiment, the bioengineering objective relates to maximizing production, the present invention contemplates that other bioengineering objectives can be used. In such instances, instead of determining or selecting a maximum yield, a separate and appropriate objective or constraint can be used.

Identification of the minimum number of heterologous reactions for a host organism. The next step in OptStrain uses the knowledge of the maximum theoretical yield to determine the minimum number of non-native functionalities that need to be added into a specific host organism network. Mathematically, this is achieved by first introducing a set of binary variables $y_j$ that serve as switches to turn the associated reaction fluxes $v_j$ on or off.

$$v_j^{min} \cdot y_j \leq v_j \leq v_j^{max} \cdot y_j$$

Note that the binary variable $y_j$ assumes a value of one if reaction j is active and a value of zero if it is inactive. This constraint will be imposed on only reactions associated with genes heterologous to the specified production host. The parameters $v_j^{min}$ and $v_j^{max}$ are calculated by minimizing and maximizing every reaction flux $v_j$ subject to the stoichiometry of the metabolic network (Burgard & Mamas, 2001). This leads to a Mixed Integer Linear Programming (MILP) model for finding the minimum number of genes to be added into the host organism network while meeting the yield target for the desired product. This formulation, discussed in greater detail later herein, enables the exploration of tradeoffs between the required numbers of heterologous genes versus the maximum theoretical product yield and also the iterative identification of all alternate optimal solutions. The end result of this step is a set of distinct pathways and corresponding gene complements that provide a ranked list of all alternatives for the efficient conversion of the substrate(s) into the desired product.

Incorporating the non-native reactions into the host organism's stoichiometric model. Upon identification of the appropriate host organism, the analysis proceeds with an organism-specific stoichiometric model augmented by the set of the identified non-native reactions. However, simply adding genes to a microbial production strain will not necessarily lead to the desired overproduction due to the fact that microbial metabolism is primed to be as responsive as possible to the imposed selection pressures (e.g., outgrow its competition). These survival objectives are typically in direct competition with the overproduction of targeted biochemicals. To combat this, we use our previously developed bilevel computational framework, OptKnock (Burgard et al., 2003; Pharkya et al., 2003) to eliminate all those functionalities which uncouple the cellular fitness objective, typically exemplified as the biomass yield, from the maximum yield of the product of interest.

1.2 Results

Computational results for microbial strain optimization focused on the production of hydrogen and vanillin. One skilled in the art having the benefit of this disclosure would understand the present invention is in no way limited to these particular bioengineering objectives which are merely illustrative of the present invention. The hydrogen production case study underscores the importance of investigating multiple substrates and microbial hosts to pinpoint the optimal production environment as well as the need to eliminate competing functionalities. In contrast, in the vanillin study, identifying the smallest number of non-native reactions is found to be the key challenge for strain design. A common database of reactions, as outlined in (Step 1), was constructed for both examples by pooling together metabolic pathways from the methylotroph *Methylobacterium extorquens* AM1 (Van Dien & Lindstrom, 2002) and the KEGG database (Kanehisa et al., 2004) of reactions.

1.2.1 Hydrogen Production Case Study

Figure 2:
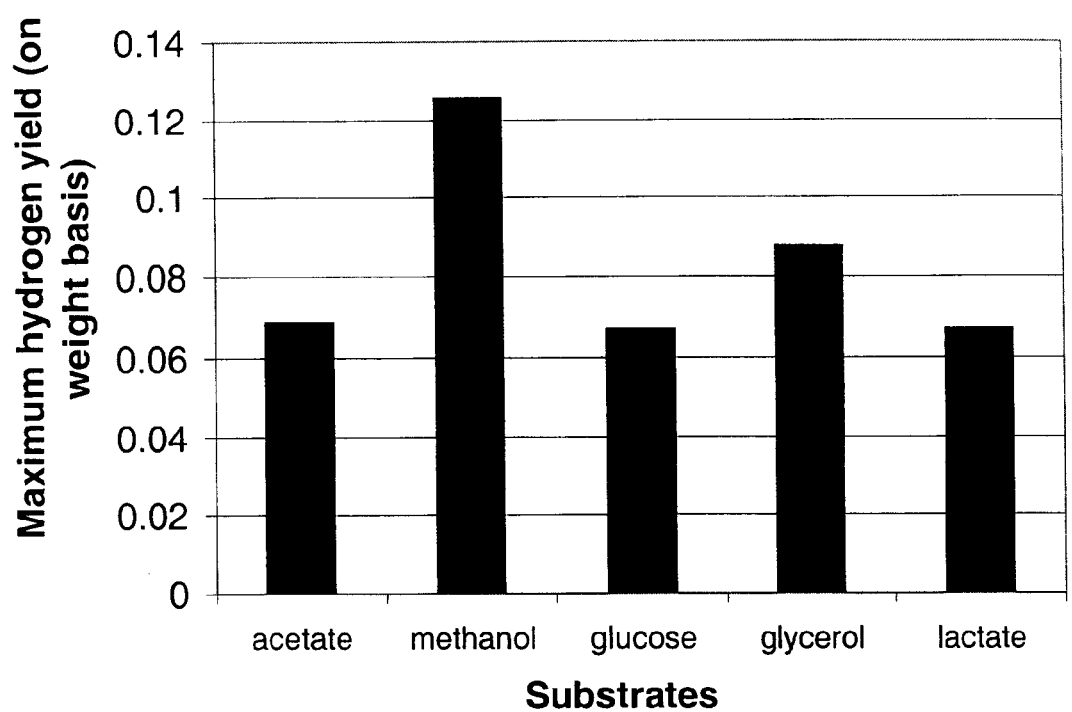
FIG. 2 is a graph indicating maximum hydrogen yield on a weight basis for different substrates.

An efficient microbial hydrogen production strategy requires the selection of an optimal substrate and a microbial strain capable of forming hydrogen at high rates. First we solved the maximum yield LP formulation (Step 2) using all catalogued reactions which were balanced with respect to hydrogen, oxygen, nitrogen, sulfur, phosphorus and carbon (approximately 3,000 reactions) as recombination candidates. Note that OptStrain allowed for different substrate choices such as pentose and hexose sugars as well as acetate, lactate, malate, glycerol, pyruvate, succinate and methanol. The highest hydrogen yield obtained for a methanol substrate was equal to 0.126 g/g substrate consumed. This is not surprising given that the hydrogen to carbon ratio for methanol is the highest at four to one. A comparison of the yields for some of the more efficient substrates is shown in FIG. 2. We decided to explore methanol and glucose further, motivated by the high yield on methanol and the favorable costs associated with the use of glucose.

The next step in the OptStrain procedure entailed the determination of the minimum number of non-native functionalities for achieving the theoretical maximum yield in a host organism. We examined three different uptake scenarios: (i) glucose as the substrate in *Escherichia coli* (an established production system), (ii) glucose in *Clostridium acetobutylicum* (a known hydrogen producer), and (iii) methanol in *Methylobacterium extorquens* (a known methanol consumer).

1.2.1.1 *Escherichia coli*

The MILP framework (described in Step 3) correctly verified that with glucose as the substrate no non-native functionalities were required by *E. coli* for hydrogen production. Interestingly, hydrogen production was possible through either the ferredoxin hydrogenase reaction (E.C.#1.12.7.2) which reduces protons to form hydrogen or via the hydrogen dehydrogenase reaction (E.C.#1.12.1.2) which converts NADH into $NAD^+$ while forming hydrogen through proton association. Subsequently, the upper and lower limits of maximum hydrogen formation were explored for the *E. coli* stoichiometric model (Reed et al., 2003) as a function of biomass formation rate (i.e., growth rate) for both aerobic and anaerobic conditions and a basis glucose uptake rate of 10 mmol/gDW/hr (see FIG. 3). Notably, the maximum theoretical hydrogen yield is higher under aerobic conditions. However, only under anaerobic conditions hydrogen is formed at maximum growth (see point A, in FIG. 3) leading to a growth-coupled production mode. Note that hydrogen production takes place through the formate hydrogen lyase reaction which converts formate into hydrogen and carbon dioxide under anaerobic conditions, in agreement with current experimental observations (Nandi & Sengupta., 1998).

Moving to phenotype restriction to curtail byproduct formation (Step 4), we explored whether the production of hydrogen in the wild type *E. coli* network (Reed et al., 2003) could be enhanced by removing functionalities from the network that were in direct or indirect competition with hydrogen production. To this end, we employed the OptKnock framework (Burgard et al., 2003; Pharkya et al., 2003), to pinpoint gene deletion strategies that couple hydrogen production with growth. Here we highlight two of the identified strategies. The first (double deletion) removes both enolase (E.C.#4.2.1.11) and glucose 6-phosphate dehydrogenase (E.C.#1.1.1.49). The removal of the enolase reaction strongly promotes hydrogen formation by directing the glycolytic flux towards the 3-phosphoglycerate branching point into the serine biosynthesis pathway. Subsequently, serine participates in a series of reactions in one-carbon metabolism to form 10-formyltetrahydrofolate which eventually is converted to formate and tetrahydrofolate. The elimination of dehydrogenase reaction prevents the shunting of any glucose 6-phosphate flux into the pentose phosphate pathway. The second strategy, a three-reaction deletion study, involves the removal of ATP synthase (E.C.#3.6.3.14), alpha-ketoglutarate dehydrogenase, and acetate kinase (E.C.#2.7.2.1). The removal of the first reaction enhances proton availability whereas the other two deletions ensure that maximum carbon flux is directed towards pyruvate which is then converted into formate through pyruvate formate lyase. Formate is catabolized into hydrogen and carbon dioxide through formate hydrogen lyase.

Figure 3:
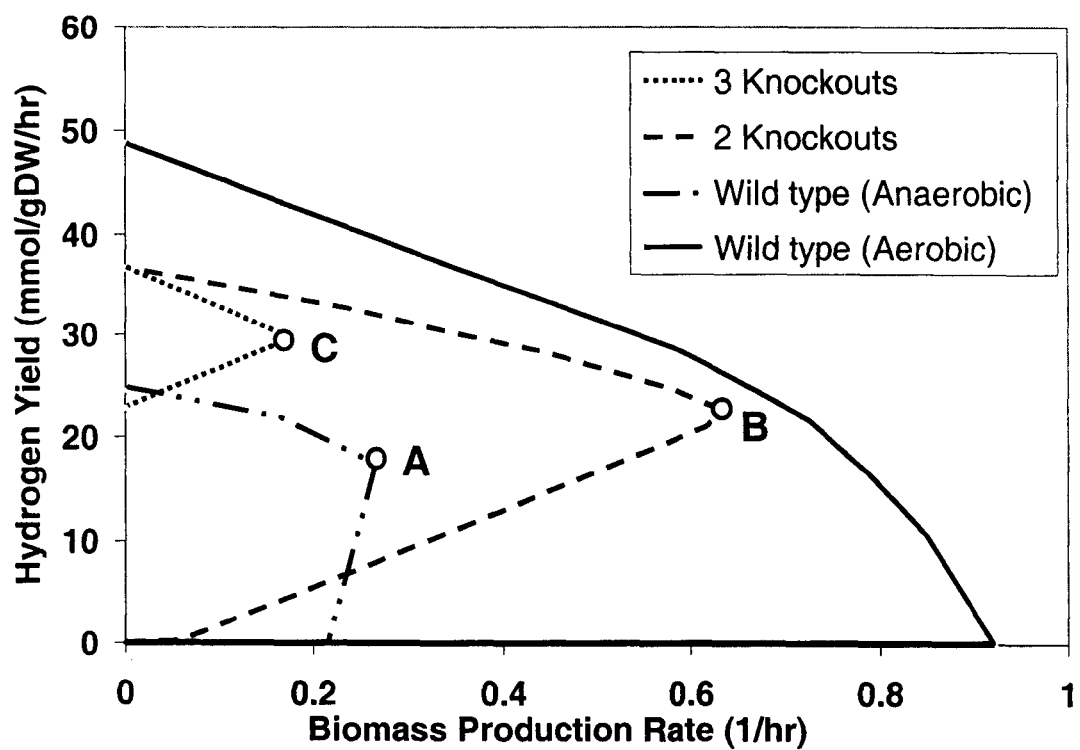
FIG. 3 is a graph illustrating hydrogen production envelopes as a function of the biomass production rate of the wild-type E. coli network under aerobic and anaerobic conditions as well as the two-reaction and three-reaction deletion mutant networks. The basis glucose uptake rate is fixed at 10 mmol/gDW/hr. These curves are constructed by finding the maximum and minimum hydrogen production rates under different rates of biomass formation. Point A denotes the required theoretical hydrogen production rate at the maximum biomass formation rate of the wild-type network under anaerobic conditions. Points B and C identify the theoretical hydrogen production rates at maximum growth for the two mutant networks respectively after fixing the corresponding carbon dioxide transport rates at the values suggested by OptKnock.

A comparison of the hydrogen production limits as a function of growth rate for both the wild-type and mutant networks is shown in FIG. 3. The transport rates of carbon dioxide for the mutant networks were fixed at the values suggested by OptKnock, thus setting the operational imperatives (Pharkya et al., 2003). Note that while the two-reaction deletion mutant has a theoretical hydrogen production rate of 22.7 mmol/gDW/hr (0.025 g/g glucose) at the maximum growth rate (Point B), the three-reaction deletion mutant produces a maximum of 29.5 mmol/gDW/hr (0.033 g/g glucose) (Point C) at the expense of a reduced maximum growth rate. Interestingly, in both mutant networks, maximum hydrogen production requires the uptake of oxygen. This is in contrast to the wild-type case where the lack of oxygen was preferred for hydrogen formation. Notably, it has been reported (Nandi & Sengupta, 1996) that although formate hydrogen lyase can only be induced in the absence of oxygen, it can function in aerobic environments. This will have to be accounted for in any experimental study conducted on the basis of these results.

1.2.1.2 *Clostridium acetobutylicum*

Ample literature evidence has identified the organisms of the *Clostridium* species as natural hydrogen production systems (Nandi & Sengupta, 1998; Katakoka et al., 1997; Chin et al., 2003; Das & Veziroglu, 2001). The reduction of protons into hydrogen through ferredoxin hydrogenase (E.C.#1.12.7.2) is the key associated reaction. Not surprisingly, using OptStrain (Step 3), we verified that no non-native reactions were required for hydrogen production (Papoutsakis & Meyer, 1985) in *Clostridium acetobultylicum* with glucose as a substrate. We next explored, as in the *E. coli* case, whether hydrogen production could be enhanced by judiciously removing competing functionalities using the OptKnock framework. To this end, we used the stoichiometric model for *Clostridium acetobutylicum* developed by Papoutsakis and coworkers (Desai et al., 1999; Papoutsakis, 1984). OptKnock suggested the deletion of the acetate-forming and butyrate-transport reactions.

Figure 4:
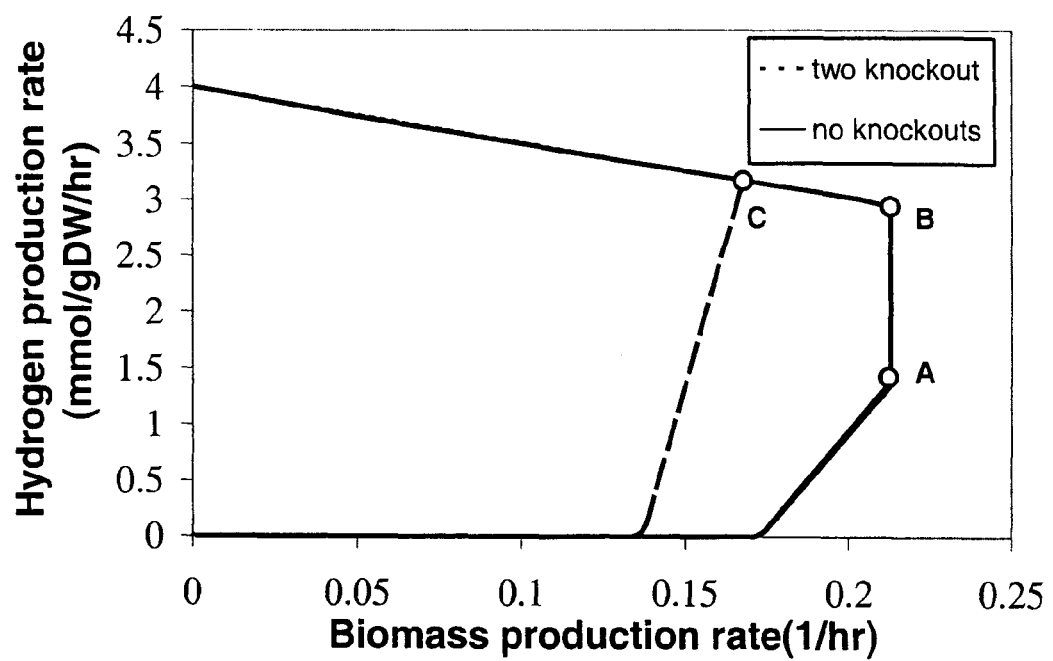
FIG. 4 is a graph illustrating hydrogen formation limits of the wild-type (solid) and mutant (dotted) Clostridium acetobutylicum metabolic network for a basis glucose uptake rate of 1 mmol/gDW/hr. Line AB denotes different alternate maximum biomass yield solutions that are available to the wild-type network. Point C pinpoints the hydrogen yield of the mutant network at maximum growth. This can be contrasted with the reported experimental hydrogen yield (2 mol/mol glucose) in C. acetobutylicum (45).

This deletion strategy is reasonable in hindsight upon considering the energetics of the entire network. Specifically, in the wild-type case the formation and secretion of each butyrate molecule requires the consumption of 2 NADH molecules, thus reducing the hydrogen production capacity of the network. However, if butyrate is not secreted, but is instead recycled to form acetone and butyryl CoA, then butyryl CoA can again be converted to butyrate without any NADH consumption. The double deletion mutant has a theoretical hydrogen yield of 3.17 mol/mol glucose (0.036 g/g glucose) at the expense of slightly lower growth rate (point C in FIG. 4). Notably, in this case, biomass formation and hydrogen production are tightly coupled, in contrast to the wild-type network where a range (1.38-2.96 mmol/gDW/hr) of hydrogen formation rates are possible (Line AB in FIG. 4) at the maximum growth rate. Experimental results (Nandi & Sengupta, 1998) indicate that only up to 2 mol of hydrogen can be produced per mol of glucose anaerobically in *Clostridium*. In fact, it has been reported that inhibitory effects of butyrate directly on hydrogen production and indirect effects of acetate on growth inhibition (Chin et al., 2003) are responsible for the observed low hydrogen yields. Interestingly, the suggested reaction eliminations directly circumvent these inhibition bottlenecks.

1.2.1.3 *Methylobacterium extorquens* AM1

Moving from glucose to methanol as the substrate, we next investigated hydrogen production in *Methylobacterium extorquens* AM1, a facultative methylotroph capable of surviving solely on methanol as a carbon and energy source (Van Dien & Lidstrom, 2002). The organism has been well-studied (Anthony, 1982; Chistoserdova et al., 2004; Chistoserdova et al., 1998; Korotkova et al., 2002; Van Dien et al., 2003) and recently, a stoichiometric model of its central metabolism was published (Van Dien & Lidstrom, 2002). Using Step 3 of OptStrain, we identified that only a single reaction needs to be introduced into the metabolic network of *M. extorquens* to enable hydrogen production. Two such candidates are hydrogenase (E.C.#1.12.7.2) which reduces protons to hydrogen or alternatively $N_5$, $N_{10}$-methyltetrahydromethanopterin hydrogenase which catalyzes the following transformation: E.C.#1.12.98.2: 5,10-Methylenetrahydromethanopterin↔ 5,10-Methenyltetrahydromethanopterin+$H_2$.

The need for an additional reaction is expected because the central metabolic pathways in the methylotroph, as abstracted in (Van Dien & Lidstrom, 2002), do not include any reactions that convert protons into hydrogen such as the hydrogenases found in *E. coli* and the anaerobes of the *Clostridia* species. Therefore, it is not surprising that, to the best of our knowledge, no one has achieved hydrogen production using methylotrophs such as *Pseudomonas* AM1 and *P. methylica* (Nandi & Sengupta, 1998). The identified reaction additions provide a plausible explanation for this outcome by pinpointing the lack of a mechanism to convert the generated protons to hydrogen.

1.2.2 Vanillin Production Case Study

Vanillin is an important flavor and aroma molecule. The low yields of vanilla from cured vanilla pods have motivated efforts for its biotechnological production. In this case study, we identify metabolic network redesign strategies for the de novo production of vanillin from glucose in *E. coli*. Using OptStrain, we first determined the maximum theoretical yield of vanillin from glucose to be 0.63 g/g glucose by solving the LP optimization over approximately 4,000 candidate reactions balanced with respect to all elements but hydrogen (Step 2). We next identified that the minimum number of non-native reactions that must be recombined into *E. coli* to endow it with the pathways necessary to achieve the maximum yield is three (Step 3). Numerous alternative pathways, differing only in their cofactor usage, which satisfy both the optimality criteria of yield and minimality of recombined reactions, were identified. For example, one such pathway uses the following three non-native reactions:

(i) E.C.#1.2.1.46: Formate+NADH+$H^+$↔Formaldehyde+$NAD^+$+$H_2O$,
(ii) E.C.#1.2.3.12: 3,4-dihydroxybenzoate (or protocatechuate)+$NAD^+$+$H_2O$+Formaldehyde↔Vanillate+$O_2$+NADH, and
(iii) E.C.#1.2.1.67: Vanillate+NADH+$H^+$↔Vanillin+$NAD^+$+$H_2O$.

Interestingly, these steps are essentially the same as those used in the experimental study by Li and Frost (1998) to convert glucose to vanillin in recombinant *E. coli* cells demonstrating that the computational procedure can indeed uncover relevant engineering strategies. Note, however, that the reported experimental yield of 0.15 g/g glucose is far from the maximum theoretical yield (i.e., 0.63 g/g glucose) of the network indicating the potential for considerable improvement.

This motivates examining whether it is possible to reach higher yields of vanillin by systematically pruning the metabolic network using OptKnock (Step 4). Here the genome-scale model of *E. coli* metabolism, augmented with the three functionalities identified above, is integrated into the Opt-Knock framework to determine the set(s) of reactions whose deletion would force a strong coupling between growth and vanillin production. The highest vanillin-yielding single, double, and quadruple knockout strategies are discussed next for a basis glucose uptake rate of 10 mmol/gDW/hr. In all cases, anaerobic conditions are selected by OptKnock as the most favorable for vanillin production. It is worth emphasizing that, in general, the deletion strategies identified by Opt-Strain are dependent upon the specific gene addition strategy fed into Step 4 of OptStrain. Accordingly, we tested whether alternative and possibly better, deletion strategies would accompany some of the other candidate addition strategies alluded to above. For the vanillin case study, we found the deletion suggestions and anticipated vanillin yields at maximal growth to be quite similar regardless of the gene addition strategy employed.

The first deletion strategy identified by OptStrain suggests removing acetaldehyde dehydrogenase (E.C.#1.2.1.10) to prevent the conversion of acetyl-CoA into ethanol. Vanillin production in this network, at the maximum biomass production rate of 0.205 $hr^{-1}$, is 3.9 mmol/gDW/hr or 0.33 g/g glucose based on the assumed uptake rate of glucose. In this deletion strategy, flux is redirected through the vanillin precursor metabolites, phosphoenolpyruvate (PEP) and erythrose-4-phosphate (E4P), by blocking the loss of carbon through ethanol secretion. The second (double) deletion strategy involves the additional removal of glucose-6-phosphate isomerase (E.C.#5.3.1.9) essentially blocking the upper half of glycolysis. These deletions cause the network to place a heavy reliance on the Entner-Doudoroff pathway to generate pyruvate and glyceraldehyde-3-phosphate (GAP) which undergoes further conversion into PEP in the lower half of glycolysis. Fructose-6-phosphate (F6P), produced through the non-oxidative part of the pentose phosphate pathway, is subsequently converted to E4P. Vanillin production, at the expense of a reduced maximum growth rate of 0.06 $hr^{-1}$, is increased to 4.78 mmol/gDW/hr or 0.40 g/g glucose. A substantially higher level of vanillin production is predicted in the four-reaction deletion mutant network without imposing a high penalty on the growth rate. This strategy leads to the production of 6.79 mmol/gDW/hr of vanillin or 0.57 g/g glucose at the maximum growth rate of 0.052 $hr^{-1}$. The Opt-Knock framework suggests the deletion of acetate kinase (E.C.#2.7.2.1), pyruvate kinase (E.C.#2.7.1.40), the PTS transport mechanism, and fructose 6-phosphate aldolase. The first three deletions prevent leakage of flux from PEP and redirect it instead to vanillin synthesis. The elimination of fructose 6-phosphate aldolase prevents the direct conversion of F6P into GAP and dihydroxyacetone (DHA). Note that both F6P and GAP are used to form E4P in the non-oxidative branch of the pentose phosphate pathway. DHA can be further reacted to form dihydroxyacetone phosphate (DHAP) with the consumption of a PEP molecule. Thus, elimination of fructose 6-phosphate aldolase prevents the utilization of both F6P and PEP which are required for vanillin synthesis. Furthermore, a surprising network flux redistribution involves the employment of a group of reactions from one-carbon metabolism to form 10-formyltetrahydrofolate, which is subsequently converted to formaldehyde.

Figure 5:
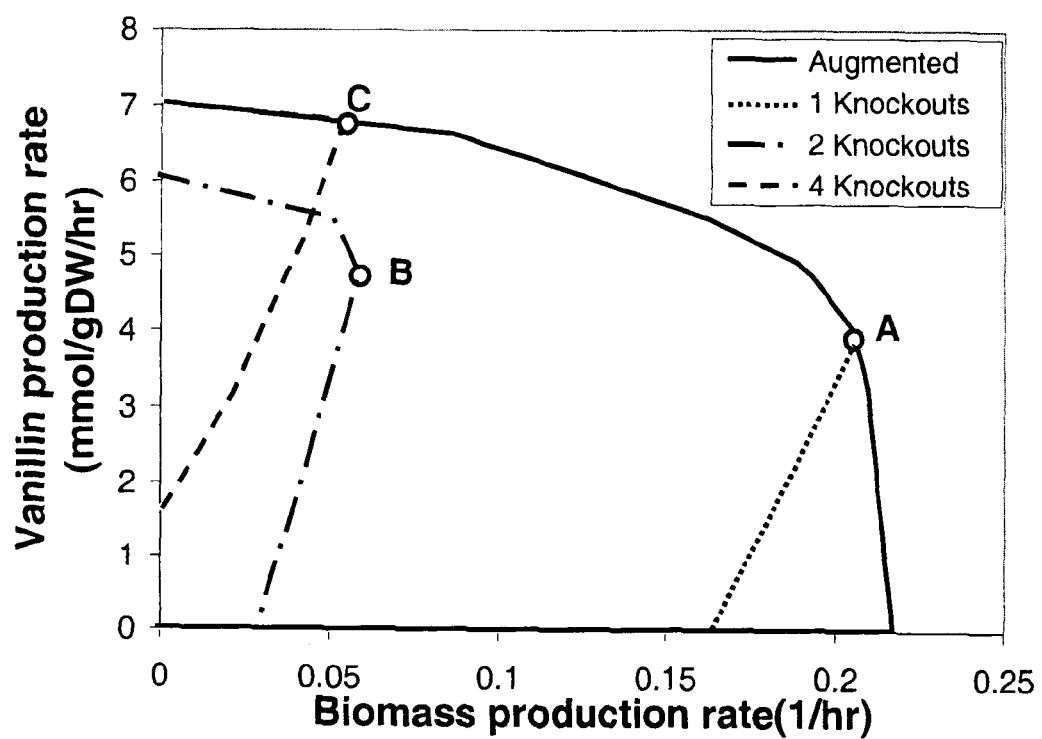
FIG. 5 is a graph illustrating vanillin production envelope of the augmented E. coli metabolic network for a basis 10 mmol/gDW/hr uptake rate of glucose. Points A, B and C denote the maximum growth points associated with the one, two and four reaction deletion mutant networks, respectively. In contrast to the wild-type network for which vanillin production is not guaranteed at any rate of biomass production, the mutant networks require significant vanillin yields to achieve high levels of biomass production. Note that an anaerobic mode of growth is suggested in all cases.

FIG. 5 compares the vanillin production envelopes, obtained by maximizing and minimizing vanillin formation at different biomass production rates for the wild-type and mutanat networks. These deletions endow the network with high levels of vanillin production under any growth conditions.

1.3 Discussion

The OptStrain framework of the present invention is aimed at systematically reshaping whole genome-scale metabolic networks of microbial systems for the overproduction of not only small but also complex molecules. We have so far examined a number of different products (e.g., 1,3 propanediol, inositol, pyruvate, electron transfer, etc.) using a variety of hosts (i.e., E. coli, C. acetobutylicum, M. extorquens). The two case studies, hydrogen and vanillin, discussed earlier show that OptStrain can address the range of challenges associated with strain redesign. At the same time, it is important to emphasize that the validity and relevance of the results obtained with the OptStrain framework are dependent on the level of completeness and accuracy of the reaction databases and microbial metabolic models considered. We have identified numerous instances of unbalanced reactions, especially with respect to hydrogen atoms, and ambiguous reaction directionality in the reaction databases that we mined. Careful curation of the downloaded reactions preceded all of our case studies. Whenever the balanceability of a reaction with respect to carbon could not be restored, the reaction was removed from consideration. We expect that this step will become less time-consuming as automated tools for reaction database testing and verification (Segre et al., 2003) are becoming available. The purely stoichiometric representation of metabolic pathways in microbial models can lead to unrealistic flux distributions by not accounting for kinetic barriers and regulatory interactions (e.g., allosteric regulation). To alleviate this, the present invention contemplates incorporating regulatory information in the form of Boolean constraints (Covert & Pals son, 2002) into the stoichiometric model of E. coli and the use of kinetic expressions on an as-needed basis (Castellanos et al. 2004; Tomita et al., 1999; Varner & Ramkrishna, 1999). Further, the present invention contemplates using OptKnock to account for not only reaction deletions but also up or down regulation of various key reaction steps. Despite these simplifications, OptStrain has already provided in many cases useful insight into microbial host redesign and, more importantly, established for the first time an integrated framework open to future modeling improvements.

It should be understood that a computer is used in implementing the methodology of the present invention. The present invention contemplates that any number of computers can be used, and any number of types of software or programming languages can be used. It should further be understood that the present invention provides for storing a representation of the networks created. The representations of the networks can be stored in a memory, in a signal, or in a bioengineered organism.

1.4 Mathematical Formulation for OptStrain

The redesign of microbial metabolic networks to enable enhanced product yields by employing the OptStrain procedure requires the solution of multiple types of optimization problems. The first optimization task (Step 2) involves determining the maximum yield of the desired product in a metabolic network comprised of a set $\mathcal{N} = \{1, \ldots, N\}$ of metabolites and a set $\mathcal{M} = \{1, \ldots, M\}$ of reactions. The Linear Programming (LP) problem for maximizing the yield on a weight basis of a particular product P (in the set $\mathcal{N} =$) from a set $\mathfrak{R}$ of substrates is formulated as:

$$\underset{v_j}{\text{Max}} \quad MW_i \cdot \sum_{j=1}^{M} S_{ij} v_j, \quad i = P$$

$$\text{subject to} \quad \sum_{j=1}^{M} S_{ij} v_j \geq 0, \quad \forall\, i \in N, i \notin \mathfrak{R} \tag{1}$$

$$\sum_{i \in \mathfrak{R}} \left( MW_i \cdot \sum_{j=1}^{M} S_{ij} v_j \right) = -1 \tag{2}$$

where $MW_i$ is the molecular weight of metabolite i, $v_j$ is the molar flux of reaction j, and $S_{ij}$ is the stoichiometric coefficient of metabolite i in reaction j. In our work, the metabolite set $\mathcal{N} =$ was comprised of approximately 4,800 metabolites and the reaction set $\mathcal{M} =$ consisted of more than 5,700 reactions. The inequality in constraint (1) allows only for secretion and prevents the uptake of all metabolites in the network other than the substrates in $\mathfrak{R}$. Constraint (2) scales the results for a total substrate uptake flux of one gram. The reaction fluxes $v_j$ can either be irreversible (i.e., $v_j \geq 0$) or reversible in which case they can assume either positive or negative values. Reactions which enable the uptake of essential-for-growth compounds such as oxygen, carbon dioxide, ammonia, sulfate and phosphate are also present.

In Step 3 of OptStrain, the minimum number of non-native reactions needed to meet the identified maximum yield from Step 2 is found. First the Universal database reactions which are absent in the examined microbial host's metabolic model are flagged as non-native. This gives rise to the following Mixed Integer Linear Programming (MILP) problem:

$$\underset{v_j, y_j}{\text{Min}} \quad \sum_{j \in M_{non-native}} y_j$$

$$\text{subject to} \quad \sum_{j=1}^{M} S_{ij} v_j \geq 0, \quad \forall\, i \in N, i \notin \mathfrak{R} \tag{1}$$

$$\sum_{i \in \mathfrak{R}} \left( MW_i \cdot \sum_{j=1}^{M} S_{ij} v_j \right) = -1, \tag{2}$$

$$MW_i \cdot \sum_{j=1}^{M} S_{ij} v_j \geq \text{Yield}^{target}, \quad i = P \tag{3}$$

$$v_j \leq v_j^{max} \cdot y_j, \quad \forall\, j \in M_{non-native} \tag{4}$$

$$v_j \geq v_j^{min} \cdot y_j, \quad \forall\, j \in M_{non-native} \tag{5}$$

$$y_j \in \{0, 1\}, \quad \forall\, j \in M_{non-native} \tag{6}$$

The set $\mathcal{M} =_{non-native}$ comprises of the non-native reactions for the examined host and is a subset of the set $\mathcal{M} =$. Constraints (1) and (2) are identical to those in the product yield maximization problem. Constraint (3) ensures that the product yield meets the maximum theoretical yield, Yield$^{target}$, calculated in step 2. The binary variables $y_j$ in constraints (4) and (5) serve as switches to turn reactions on or off. A value of zero for $y_j$ forces the corresponding flux $v_j$ to be zero, while a value of one enables it to take on nonzero values. The parameters $v_j^{min}$ and $v_j^{max}$ can either assume very low and very high values, respectively, or they can be calculated by minimizing and maximizing every reaction flux $v_j$ subject to constraints (1-3).

Alternative pathways that satisfy both optimality criteria of maximum yield and minimum non-native reactions are obtained by the iterative solution of the MILP formulation upon the accumulation of additional constraints referred to as an integer cuts. Integer cut constraints exclude from consideration all sets of reactions previously identified. For example, if a previously identified pathway utilizes reactions 1, 2, and 3, then the following constraint prevents the same reactions from being simultaneously considered in subsequent solutions: $y_1+y_2+y_3 \leq 2$. More details can be found in Burgard and Maranas (2001).

Step 4 of OptStrain identifies which reactions to eliminate from the network augmented with the non-native functionalities, using the OptKnock framework developed previously (Burgard et al., 2003; Pharkya et al., 2003). The objective of this step is to constrain the phenotypic behavior of the network so that growth is coupled with the formation of the desired biochemical, thus curtailing byproduct formation. The envelope of allowable targeted product yields versus biomass yields is constructed by solving a series of linear optimization problems which maximize and then, minimize biochemical production for various levels of biomass formation rates available to the network. More details on the optimization formulation can be found in Pharkya et al., 2003). All the optimization problems were solved in the order of minutes to hours using CPLEX 7.0 URL:ilog.com/products/eplex/) accessed via GAMS (Brooke et al., 1998) modeling environment on an IBM RS6000-270 workstation.

2. OptKnock

The ability to investigate the metabolism of single-cellular organisms at a genomic scale, and thus systemic level, motivates the need for novel computational methods aimed at identifying strain engineering strategies. The present invention includes a computational framework termed OptKnock for suggesting gene deletion strategies leading to the overproduction of specific chemical compounds in E. coli. This is accomplished by ensuring that the production of the desired chemical becomes an obligatory byproduct of growth by "shaping" the connectivity of the metabolic network. In other words, OptKnock identifies and subsequently removes metabolic reactions that are capable of uncoupling cellular growth from chemical production. The computational procedure is designed to identify not just straightforward but also non-intuitive knockout strategies by simultaneously considering the entire E. coli metabolic network as abstracted in the in silico E. coli model of Palsson and coworkers (Edwards & Palsson, 2000). The complexity and built-in redundancy of this network (e.g., the E. coli model encompasses 720 reactions) necessitates a systematic and efficient search approach to combat the combinatorial explosion of candidate gene knockout strategies.

The nested optimization framework shown in FIG. 6 is developed to identify multiple gene deletion combinations that maximally couple cellular growth objectives with externally imposed chemical production targets. This multi-layered optimization structure involving two competing optimal strategists (i.e., cellular objective and chemical production) is referred to as a bilevel optimization problem (Bard, 1998). Problem formulation specifics along with an elegant solution procedure drawing upon linear programming (LP) duality theory are described in the Methods section. The OptKnock procedure is applied to succinate, lactate, and 1,3-propanediol (PDO) production in E. coli with the maximization of the biomass yield for a fixed amount of uptaken glucose employed as the cellular objective. The obtained results are also contrasted against using the minimization of metabolic adjustment (MOMA) (Segre et al., 2002) as the cellular objective. Based on the OptKnock framework, it is possible to identify the most promising gene knockout strategies and their corresponding allowable envelopes of chemical versus biomass production in the context of succinate, lactate, and PDO production in E. coli.

A preferred embodiment of this invention describes a computational framework, termed OptKnock, for suggesting gene deletions strategies that could lead to chemical production in E. coli by ensuring that the drain towards metabolites/compounds necessary for growth resources (i.e., carbons, redox potential, and energy) must be accompanied, due to stoichiometry, by the production of the desired chemical. Therefore, the production of the desired product becomes an obligatory byproduct of cellular growth. Specifically, OptKnock pinpoints which reactions to remove from a metabolic network, which can be realized by deleting the gene(s) associated with the identified functionality. The procedure was demonstrated based on succinate, lactate, and PDO production in E. coli K-12. The obtained results exhibit good agreement with strains published in the literature. While some of the suggested gene deletions are quite straightforward, as they essentially prune reaction pathways competing with the desired one, many others are at first quite non-intuitive reflecting the complexity and built-in redundancy of the metabolic network of E. coli. For the succinate case, OptKnock correctly suggested anaerobic fermentation and the removal of the phosphotranferase glucose uptake mechanism as a consequence of the competition between the cellular and chemical production objectives, and not as a direct input to the problem. In the lactate study, the glucokinase-based glucose uptake mechanism was shown to decouple lactate and biomass production for certain knockout strategies. For the PDO case, results show that the Entner-Doudoroff pathway is more advantageous than EMP glycolysis despite the fact that it is substantially less energetically efficient. In addition, the so far popular tpi knockout was clearly shown to reduce the maximum yields of PDO while a complex network of 15 reactions was shown to be theoretically possible of "leaking" flux from the PPP pathway to the TCA cycle and thus decoupling PDO production from biomass formation. The obtained results also appeared to be quite robust with respect to the choice for the cellular objective.

The present invention contemplates any number of cellular objectives, including but not limited to maximizing a growth rate, maximizing ATP production, minimizing metabolic adjustment, minimizing nutrient uptake, minimizing redox production, minimizing a Euclidean norm, and combinations of these and other cellular objectives.

It is important to note that the suggested gene deletion strategies must be interpreted carefully. For example, in many cases the deletion of a gene in one branch of a branched pathway is equivalent with the significant up-regulation in the other. In addition, inspection of the flux changes before and after the gene deletions provides insight as to which genes need to be up or down-regulated. Lastly, the problem of mapping the set of identified reactions targeted for removal to its corresponding gene counterpart is not always uniquely specified. Therefore, careful identification of the most economical gene set accounting for isozymes and multifunctional enzymes needs to be made.

Preferably, in the OptKnock framework, the substrate uptake flux (i.e., glucose) is assumed to be 10 mmol/gDW·hr. Therefore, all reported chemical production and biomass formation values are based upon this postulated and not predicted uptake scenario. Thus, it is quite possible that the suggested deletion mutants may involve substantially lower uptake efficiencies. However, because OptKnock essentially suggests mutants with coupled growth and chemical production, one could envision a growth selection system that will successively evolve mutants with improved uptake efficiencies and thus enhanced desired chemical production characteristics.

Where there is a lack of any regulatory or kinetic information within the purely stoichiometric representation of the inner optimization problem that performs flux allocation, OptKnock is used to identify any gene deletions as the sole mechanism for chemical overproduction. Clearly, the lack of any regulatory or kinetic information in the model is a simplification that may in some cases suggest unrealistic flux distributions. The incorporation of regulatory information will not only enhance the quality of the suggested gene deletions by more appropriately resolving flux allocation, but also allow us to suggest regulatory modifications along with gene deletions as mechanisms for strain improvement. The use of alternate modeling approaches (e.g., cybernetic (Kompala et al., 1984; Ramakrishna et al., 1996; Varner and Ramkrishna, 1999), metabolic control analysis (Kacser and Burns, 1973; Heinrich and Rapoport, 1974; Hatzimanikatis et al., 1998)), if available, can be incorporated within the OptKnock framework to more accurately estimate the metabolic flux distributions of gene-deleted metabolic networks. Nevertheless, even without such regulatory or kinetic information, OptKnock provides useful suggestions for strain improvement and more importantly establishes a systematic framework. The present invention naturally contemplates future improvements in metabolic and regulatory modeling frameworks.

2.1 Methods

The maximization of a cellular objective quantified as an aggregate reaction flux for a steady state metabolic network comprising a set $\mathcal{N} = \{1, \ldots, \mathcal{N}\}$ of metabolites and a set $\mathcal{M} = \{1, \ldots, M\}$ of metabolic reactions fueled by a glucose substrate is expressed mathematically as follows, $$\text{maximize } v_{cellular\ objective} \quad \text{(Primal)}$$

$$\text{subject to } \sum_{j=1}^{M} S_{ij} v_j = 0, \quad \forall\, i \in N$$

$$v_{pts} + v_{glk} = v_{glc\_uptake} \quad \text{mmol/gDW} \cdot \text{hr}$$

$$v_{atp} \geq v_{atp\_main} \quad \text{mmol/gDW} \cdot \text{hr}$$

$$v_{biomass} \geq v_{biomass}^{target} \quad 1/\text{hr}$$

$$v_j \geq 0, \quad \forall\, j \in M_{irrev}$$

$$v_j \leq 0, \quad \forall\, j \in M_{secr\_only}$$

$$v_j \in R, \quad \forall\, j \in M_{rev}$$

where $S_{ij}$ is the stoichiometric coefficient of metabolite i in reaction j, $v_j$ represents the flux of reaction j, $v_{glc\_uptake}$ is the basis glucose uptake scenario, $v_{atp\_main}$ is the non-growth associated ATP maintenance requirement, and $v_{biomass}^{target}$ is a minimum level of biomass production. The vector v includes both internal and transport reactions. The forward (i.e., positive) direction of transport fluxes corresponds to the uptake of a particular metabolite, whereas the reverse (i.e., negative) direction corresponds to metabolite secretion. The uptake of glucose through the phosphotransferase system and glucokinase are denoted by $v_{pts}$ and $v_{glk}$, respectively. Transport fluxes for metabolites that can only be secreted from the network are members of $M_{secr\_only}$. Note also that the complete set of reactions M is subdivided into reversible $M_{rev}$ and irreversible $M_{irrev}$ reactions. The cellular objective is often assumed to be a drain of biosynthetic precursors in the ratios required for biomass formation (Neidhardt and Curtiss, 1996). The fluxes are reported per 1 gDW·hr such that biomass formation is expressed as g biomass produced/gDW·hr or 1/hr.

The modeling of gene deletions, and thus reaction elimination, first requires the incorporation of binary variables into the flux balance analysis framework (Burgard and Maranas, 2001; Burgard et al., 2001). These binary variables, $$y_j = \begin{cases} 1 & \text{if reaction flux } v_j \text{ is active} \\ 0 & \text{if reaction flux } v_j \text{ is not active} \end{cases}, \forall\, j \in M$$

assume a value of one if reaction j is active and a value of zero if it is inactive. The following constraint, $$v_j^{min} \cdot y_j \leq v_j \leq v_j^{max} \cdot y_j, \quad \forall\, j \in M$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. In this study, $v_j^{min}$ and $v_j^{max}$ are identified by minimizing and subsequently maximizing every reaction flux subject to the constraints from the Primal problem.

The identification of optimal gene/reaction knockouts requires the solution of a bilevel optimization problem that chooses the set of reactions that can be accessed ($y_j=1$) so as the optimization of the cellular objective indirectly leads to the overproduction of the chemical or biochemical of interest (see also FIG. 6). Using biomass formation as the cellular objective, this is expressed mathematically as the following bilevel mixed-integer optimization problem.

$$\begin{aligned}
&\underset{y_j}{\text{maximize}}\ v_{chemical} \quad (OptKnock) \\
&\text{subject to } \begin{pmatrix} \underset{v_j}{\text{maximize}}\ v_{biomass} & \text{(Primal)} \\ \text{subject to } \sum_{j=1}^{M} S_{ij} v_j = 0, & \forall\, i \in N \\ v_{pts} + v_{glk} = v_{glc\_uptake} & \\ v_{atp} \geq v_{atp\_main} & \end{pmatrix} \\
&\quad v_{biomass} \geq v_{biomass}^{target} \\
&\quad v_j^{min} \cdot y_j \leq v_j \leq v_j^{max} \cdot y_j, \quad \forall\, j \in M \\
&\quad y_j = \{0, 1\}, \quad \forall\, j \in M \\
&\quad \sum_{j \in M} (1 - y_j) \leq K
\end{aligned}$$

where K is the number of allowable knockouts. The final constraint ensures that the resulting network meets a minimum biomass yield, $v_{biomass}^{target}$.

The direct solution of this two-stage optimization problem is intractable given the high dimensionality of the flux space (i.e., over 700 reactions) and the presence of two nested optimization problems. To remedy this, we develop an efficient solution approach borrowing from LP duality theory which shows that for every linear programming problem (primal) there exists a unique optimization problem (dual) whose optimal objective value is equal to that of the primal problem. A similar strategy was employed by (Burgard and Maranas, 2003) for identifying/testing metabolic objective functions from metabolic flux data. The dual problem (Ignizio and Cavalier, 1994) associated with the OptKnock inner problem is $$\text{minimize } v_{atp\_main} \cdot \mu_{atp} + v_{biomass}^{target} \cdot \mu_{biomass} + v_{glc\_uptake} \cdot glc \quad (Dual)$$

$$\text{subject to } \sum_{i=1}^{N} \lambda_i^{stoich} S_{i,glk} + \mu_{glk} + glc = 0$$

-continued $$\sum_{i=1}^{N} \lambda_i^{stoich} S_{i,pts} + \mu_{pts} + glc = 0$$

$$\sum_{i=1}^{N} \lambda_i^{stoich} S_{i,biomass} + \mu_{biomass} = 1$$

$$\sum_{i=1}^{N} \lambda_i^{stoich} S_{ij} + \mu_j = 0, \quad \forall j \in M, j \neq glk, pts, biomass$$

$$\mu_j^{min} \cdot (1 - y_j) \leq \mu_j \leq \mu_j^{max} \cdot (1 - y_j), \quad \forall j \in M_{rev} \text{ and } j \notin M_{secr\_only}$$

$$\mu_j \geq \mu_j^{min} \cdot (1 - y_j), \quad \forall j \in M_{rev} \text{ and } M_{secr\_only}$$

$$\mu_j \leq \mu_j^{max} \cdot (1 - y_j), \quad \forall j \in M_{irrev} \text{ and } j \notin M_{secr\_only}$$

$$\mu_j \in R, \quad \forall j \in M_{irrev} \text{ and } M_{secr\_only}$$

$$\lambda_i^{stoich} \in R, \quad \forall j \in N$$

$$glc \in R$$

where $\lambda_i^{stoich}$ is the dual variable associated with the stoichiometric constraints, glc is the dual variable associated with the glucose uptake constraint, and $\mu_j$ is the dual variable associated with any other restrictions on its corresponding flux $v_j$ in the Primal. Note that the dual variable $\mu_j$ acquires unrestricted sign if its corresponding flux in the OptKnock inner problem is set to zero by enforcing $y_j=0$. The parameters $\mu_j^{min}$ and $\mu_j^{max}$ are identified by minimizing and subsequently maximizing their values subject to the constraints of the Dual problem.

If the optimal solutions to the Primal and Dual problems are bounded, their objective function values must be equal to one another at optimality. This means that every optimal solution to both problems can be characterized by setting their objectives equal to one another and accumulating their respective constraints. Thus the bilevel formulation for OptKnock shown previously can be transformed into the following single-level MILP maximize $V_{chemical}$ (OptKnock)

subject to $$v_{biomass} = v_{atp\_main} \cdot \mu_{atp} + v_{biomass}^{target} \cdot \mu_{biomass} + v_{glc\_uptake} \cdot glc$$

$$\sum_{j=1}^{M} S_{ij} v_j = 0, \quad \forall i \in N$$

$$v_{pts} + v_{glk} = v_{glc\_uptake} \quad \text{mmol/gDW} \cdot \text{hr}$$

$$v_{atp} \geq v_{atp\_main} \quad \text{mmol/gDW} \cdot \text{hr}$$

$$\sum_{i=1}^{N} \lambda_i^{stoich} S_{i,glk} + \mu_{glk} + glc = 0$$

$$\sum_{i=1}^{N} \lambda_i^{stoich} S_{i,pts} + \mu_{pts} + glc = 0$$

$$\sum_{i=1}^{N} \lambda_i^{stoich} S_{i,biomass} + \mu_{biomass} = 1$$

$$\sum_{i=1}^{N} \lambda_i^{stoich} S_{ij} + \mu_j = 0, \quad \forall j \in M, j \neq glk, pts, biomass$$

-continued $$\sum_{j \in M} (1 - y_j) \leq K$$

$$v_{biomass} \geq v_{biomass}^{target}$$

$$\mu_j^{min} \cdot (1 - y_j) \leq \mu_j \leq \mu_j^{max} \cdot (1 - y_j),$$

$$\forall j \in M_{rev} \text{ and } j \notin M_{secr\_only}$$

$$\mu_j \geq \mu_j^{min} \cdot (1 - y_j), \quad \forall j \in M_{rev} \text{ and } M_{secr\_only}$$

$$\mu_j \leq \mu_j^{max} \cdot (1 - y_j), \quad \forall j \in M_{irrev} \text{ and } j \notin M_{secr\_only}$$

$$\mu_j \in R, \quad \forall j \in M_{irrev} \text{ and } M_{secr\_only}$$

$$v_j^{min} \cdot y_j \leq v_j \leq v_j^{max} \cdot y_j, \quad \forall j \in M$$

$$\lambda_i^{stoich} \in R, \quad \forall j \in N$$

$$glc \in R$$

$$y_j = \{0, 1\}, \quad \forall j \in M$$

An important feature of the above formulation is that if the problem is feasible, the optimal solution will always be found. In this invention, the candidates for gene knockouts included, but are not limited to, all reactions of glycolysis, the TCA cycle, the pentose phosphate pathway, respiration, and all anaplerotic reactions. This is accomplished by limiting the number of reactions included in the summation $$\left(\text{i.e.,} \sum_{j \in Central\ Metabolism} (1 - y_j) = K\right).$$

Problems containing as many as 100 binary variables were solved in the order of minutes to hours using CPLEX 7.0 accessed via the GAMS modeling environment on an IBM RS6000-270 workstation. It should be understood, however, that the present invention is not dependent upon any particular type of computer or environment being used. Any type can be used to allow for inputting and outputting the information associated with the methodology of the present invention. Moreover, the steps of the methods of the present invention can be implemented in any number of types software applications, or languages, and the present invention is not limited in this respect. It will be appreciated that other embodiments and uses will be apparent to those skilled in the art and that the invention is not limited to these specific illustrative examples.

2.2 Example 1

Succinate and Lactate Production

Which reactions, if any, that could be removed from the *E. coli* K-12 stoichiometric model (Edwards & Pals son, 2000) so as the remaining network produces succinate or lactate whenever biomass maximization is a good descriptor of flux allocation were identified. A prespecified amount of glucose (10 mmol/gDW·hr), along with unconstrained uptake routes for inorganic phosphate, oxygen, sulfate, and ammonia are provided to fuel the metabolic network. The optimization step could opt for or against the phosphotransferase system, glucokinase, or both mechanisms for the uptake of glucose. Secretion routes for acetate, carbon dioxide, ethanol, formate, lactate and succinate are also enabled. Note that because the glucose uptake rate is fixed, the biomass and product yields are essentially equivalent to the rates of biomass and product production, respectively. In all cases, the OptKnock procedure eliminated the oxygen uptake reaction pointing at anaerobic growth conditions consistent with current succinate (Zeikus et al., 1999) and lactate (Datta et al., 1995) fermentative production strategies.

Table I summarizes three of the identified gene knockout strategies for succinate overproduction (i.e., mutants A, B, and C). The results for mutant A suggested that the removal of two reactions (i.e., pyruvate formate lyase and lactate dehydrogenase) from the network results in succinate production reaching 63% of its theoretical maximum at the maximum biomass yield. This knockout strategy is identical to the one employed by Stols and Donnelly (1997) in their succinate overproducing E. coli strain. Next, the envelope of allowable succinate versus biomass production was explored for the wild-type E. coli network and the three mutants listed in Table I. The succinate production limits revealed that mutant A does not exhibit coupled succinate and biomass formation until the yield of biomass approaches 80% of the maximum. Mutant B, however, with the additional deletion of acetaldehyde dehydrogenase, resulted in a much earlier coupling of succinate with biomass yields.

A less intuitive strategy was identified for mutant C which focused on inactivating two PEP consuming reactions rather than eliminating competing byproduct (i.e., ethanol, formate, and lactate) production mechanisms. First, the phosphotransferase system was disabled requiring the network to rely exclusively on glucokinase for the uptake of glucose. Next, pyruvate kinase was removed leaving PEP carboxykinase as the only central metabolic reaction capable of draining the significant amount of PEP supplied by glycolysis. This strategy, assuming that the maximum biomass yield could be attained, resulted in a succinate yield approaching 88% of the theoretical maximum. In addition, there was significant succinate production for every attainable biomass yield, while the maximum theoretical yield of succinate is the same as that for the wild-type strain.

The OptKnock framework was next applied to identify knockout strategies for coupling lactate and biomass production. Table I shows three of the identified gene knockout strategies (i.e., mutants A, B, and C). Mutant A redirects flux toward lactate at the maximum biomass yield by blocking acetate and ethanol production. This result is consistent with previous work demonstrating that an adh, pta mutant E. coli strain could grow anaerobically on glucose by producing lactate (Gupta & Clark, 1989). Mutant B provides an alternate strategy involving the removal of an initial glycolysis reaction along with the acetate production mechanism. This results in a lactate yield of 90% of its theoretical limit at the maximum biomass yield. It is also noted that the network could avoid producing lactate while maximizing biomass formation. This is due to the fact that OptKnock does not explicitly account for the "worst-case" alternate solution. It should be appreciated that upon the additional elimination of the glucokinase and ethanol production mechanisms, mutant C exhibited a tighter coupling between lactate and biomass production.

TABLE I

Biomass and chemical yields for various gene knockout strategies identified by OptKnock. The reactions and corresponding enzymes for each knockout strategy are listed.

Succinate

| ID | | Knockouts | Enzyme | max $v_{biomass}$ Biomass (1/hr) | max $v_{biomass}$ Succinate (mmol/hr) | min $\boxtimes\Sigma(v_0 - v)^2$ Succinate (mmol/hr) |
|---|---|---|---|---|---|---|
| Wild | | "Complete network" | | 0.38 | 0.12 | 0 |
| A | 1 | COA + PYR → ACCOA + FOR | Pyruvate formate lyase | 0.31 | 10.70 | 1.65 |
| | 2 | NADH + PYR ↔ LAC + NAD | Lactate dehydrogenase | | | |
| B | 1 | COA + PYR → ACCOA + FOR | Pyruvate formate lyase | 0.31 | 10.70 | 4.79 |
| | 2 | NADH + PYR ↔ LAC + NAD | Lactate dehydrogenase | | | |
| | 3 | ACCOA + 2 NADH ↔ COA + ETH + 2 NAD | Acetaldehyde dehydrogenase | | | |
| C | 1 | ADP + PEP → ATP + PYR | Pyruvate kinase | 0.16 | 15.15 | 6.21 |
| | 2 | ACTP + ADP ↔ AC + ATP or | Acetate kinase | | | |
| | | ACCOA + Pi ↔ ACTP + COA | Phosphotransacetylase | | | |
| | 3 | GLC + PEP → G6P + PYR | Phosphotransferase system | | | |

Lactate

| ID | | Knockouts | Enzyme | max $v_{biomass}$ Biomass (1/hr) | max $v_{biomass}$ Lactate (mmol/hr) | min $\boxtimes\Sigma(v_0 - v)^2$ Lactate (mmol/hr) |
|---|---|---|---|---|---|---|
| Wild | | "Complete network" | | 0.38 | 0 | 0 |
| A | 1 | ACTP + ADP ↔ AC + ATP or | Acetate kinase | 0.28 | 10.46 | 5.58 |
| | | ACCOA + Pi ↔ ACTP + COA | Phosphotransacetylase | | | |
| | 2 | ACCOA + 2 NADH ↔ COA + ETH + 2 NAD | Acetaldehyde dehydrogenase | | | |
| B | 1 | ACTP + ADP ↔ AC + ATP or | Acetate kinase | 0.13 | 18.00 | 0.19 |
| | | ACCOA + Pi ↔ ACTP + COA | Phosphotransacetylase | | | |
| | 2 | ATP + F6P → ADP + FDP or | Phosphofructokinase | | | |
| | | FDP ↔ T3P1 + T3P2 | Fructose-1,6-bisphosphatate aldolase | | | |
| C | 1 | ACTP + ADP ↔ AC + ATP or | Acetate kinase | 0.12 | 18.13 | 10.53 |
| | | ACCOA + Pi ↔ ACTP + COA | Phosphotransacetylase | | | |
| | 2 | ATP + F6P → ADP + FDP or | Phosphofructokinase | | | |

TABLE I-continued

Biomass and chemical yields for various gene knockout strategies identified by OptKnock.
The reactions and corresponding enzymes for each knockout strategy are listed.

|   |   | FDP ↔ T3P1 + T3P2 | Fructose-1,6-bisphosphatate aldolase |
|---|---|---|---|
|   | 3 | ACCOA + 2 NADH ↔ COA + ETH + 2 NAD | Acetaldehyde dehydrogenase |
|   | 4 | GLC + ATP → G6P + PEP | Glucokinase |

1,3-Propanediol

| | | | | max $v_{biomass}$ | | min $\mathbb{K}\Sigma(v_0 - v)^2$ |
|---|---|---|---|---|---|---|
| ID | | Knockouts | Enzyme | Biomass (1/hr) | 1,3-PD (mmol/hr) | 1,3-PD (mmol/hr) |
| Wild | | "Complete network" | | 1.06 | 0 | 0 |
| A | 1 | FDP → F6P + Pi or | Fructose-1,6-bisphosphatase | 0.21 | 9.66 | 8.66 |
|   |   | FDP ↔ T3P1 + T3P2 | Fructose-1,6-bisphosphate aldolase | | | |
|   | 2 | 13PGD + ADP ↔ 3PG + ATP or | Phosphoglycerate kinase | | | |
|   |   | NAD + Pi + T3P1 ↔ 13PDG + NADH | Glyceraldehyde-3-phosphate dehydrogenase | | | |
|   | 3 | GL + NAD ↔ GLAL + NADH | Aldehyde dehydrogenase | | | |
| B | 1 | T3P1 ↔ T3P2 | Triosphosphate isomerase | 0.29 | 9.67 | 9.54 |
|   | 2 | G6P + NADP ↔ D6PGL + NADPH or | Glucose 6-phosphate-1-dehydrogenase | | | |
|   |   | D6PGL → D6PGC | 6-Phosphogluconolactonase | | | |
|   | 3 | DR5P → ACAL + T3P1 | Deoxyribose-phosphate aldolase | | | |
|   | 4 | GL + NAD ↔ GLAL + NADH | Aldehyde dehydrogenase | | | |

The maximum biomass and corresponding chemical yields are provided on a basis of 10 mmol/hr glucose fed and 1 gDW of cells. The rightmost column provides the chemical yields for the same basis assuming a minimal redistribution of metabolic fluxes from the wild-type (undeleted) *E. coli* network (MOMA assumption). For the 1,3-propanediol case, glycerol secretion was disabled for both knockout strategies.

2.2 Example 2

1,3-Propanediol (PDO) Production

In addition to devise optimum gene knockout strategies, OptKnock was used to design strains where gene additions were needed along with gene deletions such as in PDO production in *E. coli*. Although microbial 1,3-propanediol (PDO) production methods have been developed utilizing glycerol as the primary carbon source (Hartlep et al., 2002; Zhu et al., 2002), the production of 1,3-propanediol directly from glucose in a single microorganism has recently attracted considerable interest (Cameron et al., 1998; Biebl et al., 1999; Zeng & Biebl, 2002). Because wild-type *E. coli* lacks the pathway necessary for PDO production, the gene addition framework was first employed (Burgard and Maranas, 2001) to identify the additional reactions needed for producing PDO from glucose in *E. coli*. The gene addition framework identified a straightforward three-reaction pathway involving the conversion of glycerol-3-P to glycerol by glycerol phosphatase, followed by the conversion of glycerol to 1,3 propanediol by glycerol dehydratase and 1,3-propanediol oxidoreductase. These reactions were then added to the *E. coli* stoichiometric model and the OptKnock procedure was subsequently applied.

OptKnock revealed that there was neither a single nor a double deletion mutant with coupled PDO and biomass production. However, one triple and multiple quadruple knockout strategies that can couple PDO production with biomass production was identified. Two of these knockout strategies are shown in Table I. The results suggested that the removal of certain key functionalities from the *E. coli* network resulted in PDO overproducing mutants for growth on glucose. Specifically, Table I reveals that the removal of two glycolytic reactions along with an additional knockout preventing the degradation of glycerol yields a network capable of reaching 72% of the theoretical maximum yield of PDO at the maximum biomass yield. Note that the glyceraldehyde-3-phosphate dehydrogenase (gapA) knockout was used by DuPont in their PDO-overproducing *E. coli* strain (Nakamura, 2002). Mutant B revealed an alternative strategy, involving the removal of the triose phosphate isomerase (tpi) enzyme exhibiting a similar PDO yield and a 38% higher biomass yield. Interestingly, a yeast strain deficient in triose phosphate isomerase activity was recently reported to produce glycerol, a key precursor to PDO, at 80-90% of its maximum theoretical yield (Compagno et al., 1996).

Review of the flux distributions of the wild-type *E. coli*, mutant A, and mutant B networks that maximize the biomass yield indicates that, not surprisingly, further conversion of glycerol to glyceraldehyde was disrupted in both mutants A and B. For mutant A, the removal of two reactions from the top and bottom parts of glycolysis resulted in a nearly complete inactivation of the pentose phosphate and glycolysis (with the exception of triose phosphate isomerase) pathways. To compensate, the Entner-Doudoroff glycolysis pathway is activated to channel flux from glucose to pyruvate and glyceraldehyde-3-phosphate (GAP). GAP is then converted to glycerol which is subsequently converted to PDO. Energetic demands lost with the decrease in glycolytic fluxes from the wild-type *E. coli* network case, are now met by an increase in the TCA cycle fluxes. The knockouts suggested for mutant B redirect flux toward the production of PDO by a distinctly different mechanism. The removal of the initial pentose phosphate pathway reaction results in the complete flow of metabolic flux through the first steps of glycolysis. At the fructose bisphosphate aldolase junction, the flow is split into the two product metabolites: dihydroxyacetone-phosphate (DHAP) which is converted to PDO and GAP which continues through the second half of the glycolysis. The removal of the triose-phosphate isomerase reaction prevents any interconversion between DHAP and GAP. Interestingly, a fourth knockout is predicted to retain the coupling between biomass formation and chemical production. This knockout prevents the "leaking" of flux through a complex pathway involving 15 reactions that together convert ribose-5-phosphate (R5P) to acetate and GAP, thereby decoupling growth from chemical production.

Next, the envelope of allowable PDO production versus biomass yield is explored for the two mutants listed in Table I. The production limits of the mutants along with the original

*E. coli* network, reveal that the wild-type *E. coli* network has no "incentive" to produce PDO if the biomass yield is to be maximized. On the other hand, both mutants A and B have to produce significant amounts of PDO if any amount of biomass is to be formed given the reduced functionalities of the network following the gene removals. Mutant A, by avoiding the tpi knockout that essentially sets the ratio of biomass to PDO production, is characterized by a higher maximum theoretical yield of PDO. The above described results hinge on the use of glycerol as a key intermediate to PDO. Next, the possibility of utilizing an alternative to the glycerol conversion route for 1,3-propandediol production was explored.

Applicants identified a pathway in *Chloroflexus aurantiacus* involving a two-step NADPH-dependant reduction of malonyl-CoA to generate 3-hydroxypropionic acid (3-HPA) (Menendez et al., 1999; Hugler et al., 2002). 3-HPA could then be subsequently converted chemically to 1,3 propanediol given that there is no biological functionality to achieve this transformation. This pathway offers a key advantage over PDO production through the glycerol route because its initial step (acetyl-CoA carboxylase) is a carbon fixing reaction. Accordingly, the maximum theoretical yield of 3-HPA (1.79 mmol/mmol glucose) is considerably higher than for PDO production through the glycerol conversion route (1.34 mmol/mmol glucose). The application of the OptKnock framework upon the addition of the 3-HPA production pathway revealed that many more knockouts are required before biomass formation is coupled with 3-HPA production. One of the most interesting strategies involves nine knockouts yielding 3-HPA production at 91% of its theoretical maximum at optimal growth. The first three knockouts were relatively straightforward as they involved removal of competing acetate, lactate, and ethanol production mechanisms. In addition, the Entner-Doudoroff pathway (either phosphogluconate dehydratase or 2-keto-3-deoxy-6-phosphogluconate aldolase), four respiration reactions (i.e., NADH dehydrogenase I, NADH dehydrogenase II, glycerol-3-phosphate dehydrogenase, and the succinate dehydrogenase complex), and an initial glycolyis step (i.e., phosphoglucose isomerase) are disrupted. This strategy resulted in a 3-HPA yield that, assuming the maximum biomass yield, is 69% higher than the previously identified mutants utilizing the glycerol conversion route.

2.3 Example 3

Alternative Cellular Objective: Minimization of Metabolic Adjustment

All results described previously were obtained by invoking the maximization of biomass yield as the cellular objective that drives flux allocation. This hypothesis essentially assumes that the metabolic network could arbitrarily change and/or even rewire regulatory loops to maintain biomass yield maximality under changing environmental conditions (maximal response). Recent evidence suggests that this is sometimes achieved by the K-12 strain of *E. coli* after multiple cycles of growth selection (Ibarra et al., 2002). In this section, a contrasting hypothesis was examined (i.e., minimization of metabolic adjustment (MOMA) (Segre et al., 2002)) that assumed a myopic (minimal) response by the metabolic network upon gene deletions. Specifically, the MOMA hypothesis suggests that the metabolic network will attempt to remain as close as possible to the original steady state of the system rendered unreachable by the gene deletion(s). This hypothesis has been shown to provide a more accurate description of flux allocation immediately after a gene deletion event (Segre et al., 2002). For this study, the MOMA objective was utilized to predict the flux distributions in the mutant strains identified by OptKnock. The base case for the lactate and succinate simulations was assumed to be maximum biomass formation under anaerobic conditions, while the base case for the PDO simulations was maximum biomass formation under aerobic conditions. The results are shown in the last column of Table 1. In all cases, the suggested multiple gene knock-out strategy suggests only slightly lower chemical production yields for the MOMA case compared to the maximum biomass hypothesis. This implies that the OptKnock results are fairly robust with respect to the choice of cellular objective.

3.0 Alternative Embodiments

The publications and other material used herein to illuminate the background of the invention or provide additional details respecting the practice, are herein incorporated by reference in their entirety. The present invention contemplates numerous variations, including variations in organisms, variations in cellular objectives, variations in bioengineering objectives, variations in types of optimization problems formed and solutions used. These and/or other variations, modifications or alterations may be made therein without departing from the spirit and the scope of the invention as set forth in the appended claims.

REFERENCES

Anthony, C. (1982) The Biochemistry of Methylotrophs (Academic Press.)
Arita, M. (2000) Simulation Practice and Theory 8, 109-125.
Arita, M. (2004) Proc Natl Acad Sci USA 101, 1543-7.
Badarinarayana, V., Estep, P. W., 3rd, Shendure, J., Edwards, J., Tavazoie, S., Lam, F., Church, G. M. (2001) Nat Biotechnol 19(11): 1060-5.
Bailey, J. E. (1991) Science 252, 1668-75.
Bailey, J. E. (2001) Nat Biotechnol 19, 503-4.
Bard, J. F. 1998. Practical bilevel optimization: algorithms and applications. Dordrecht; Boston, Kluwer Academic.
Biebl, H., Menzel, K., Zeng, A. P., Deckwer, W. D. (1999) Appl Environ Microbiol 52: 289-297.
Bond, D. R. & Lovley, D. R. (2003) Appl Environ Microbiol 69, 1548-55.
Bond, D. R., Holmes, D. E., Tender, L. M. & Lovley, D. R. (2002) Science 295, 483-5.
Brown, M. (1999) Perl programmer's reference (Osborne/McGraw-Hill, Berkeley, Calif.).
Burgard, A. P. & Maranas, C. D. (2001) Biotechnol Bioeng 74, 364-375.
Burgard, A. P., Pharkya, P. & Maranas, C. D. (2003) Biotechnol Bioeng 84, 647-57.
Burgard, A. P., Maranas, C. D. (2003) Biotechnol Bioeng 82(6): 670-7.
Burgard, A. P., Vaidyaraman, S., Maranas, C. D. (2001) Biotechnol Prog 17: 791-797.
Cameron, D. C., Altaras, N. E., Hoffman, M. L., Shaw, A. J. (1998) Biotechnol Prog 14(1): 116-25.
Castellanos, M., Wilson, D. B. & Shuler, M. L. (2004) Proc Natl Acad Sci USA 101, 6681-6.
Causey, T. B., Shanmugam, K. T., Yomano, L. P. & Ingram, L. O. (2004) Proc Natl Acad Sci USA 101, 2235-40.
Chin, H. L., Chen, Z. S. & Chou, C. P. (2003) Biotechnol Prog 19, 383-8.
Chistoserdova, L., Laukel, M., Portais, J. C., Vorholt, J. A. & Lidstrom, M. E. (2004) J Bacteriol 186, 22-8.

Chistoserdova, L., Vorholt, J. A., Thauer, R. K. & Lidstrom, M. E. (1998) Science 281, 99-102.
Compagno, C., Boschi, F., Ranzi, B. M. (1996) Biotechnol Prog 12(5): 591-5.
Covert, M. W., Palsson, B. O. (2002) J Biol Chem 277(31): 28058-64.
Covert, M. W., Schilling, C. H., & Palsson, B. O. (2001) J Theor Biol 213(1): 73-88.
Das, D. & Veziroglu, T. N. (2001) International Journal of Hydrogen Energy 26, 13-28.
Datta, R., Tsai, S., Bonsignore, P., Moon, S., Frank, J. R. (1995) FEMS Microbiol. Rev. 16: 221-231.
David, H., Akesson, M. & Nielsen, J. (2003) Eur J Biochem 270, 4243-53.
Desai, R. P., Nielsen, L. K. & Papoutsakis, E. T. (1999) J Biotechnol 71, 191-205.
Edwards, J. S. & Palsson, B. O. (2000) Proc Natl Acad Sci USA 97, 5528-33.
Edwards, J. S., Ibarra, R. U., Palsson, B. O. (2001) Nat Biotechnol 19(2): 125-30.
Edwards, J. S., Palsson, B. O. (2000) Proc Natl Acad Sci USA 97(10): 5528-33.
Ellis, L. B., Hou, B. K., Kang, W. & Wackett, L. P. (2003) Nucleic Acids Res 31, 262-5.
Eppstein, D. (1994) in 35th IEEE Symp. Foundations of Comp. Sci, Santa Fe), pp. 154-165.
Fan, L. T., Bertok, B. & Friedler, F. (2002) Comput Chem 26, 265-92.
Finneran, K. T., Housewright, M. E. & Lovley, D. R. (2002) Environ Microbiol 4, 510-6.
Forster, J., Famili, I., Fu, P. C., Palsson, B., Nielsen, J. (2003) Genome Research 13(2): 244-253.
Forster, J., Famili, I., Fu, P., Palsson, B. O. & Nielsen, J. (2003) Genome Res 13, 244-53.
Gupta, S., Clark, D. P. (1989) J Bacteriol 171(7): 3650-5.
Hartlep, M., Hussmann, W., Prayitno, N., Meynial-Salles, I., Zeng, A. P. (2002) Appl Microbiol Biotechnol 60(1-2): 60-6.
Hatzimanikatis, V., Emmerling, M., Sauer, U., Bailey, J. E. (1998) Biotechnol Bioeng 58(2-3): 154-61.
Hatzimanikatis, V., Li, C., Ionita, J. A. & Broadbelt, L. J. (2003) presented at Biochemical Engineering XIII Conference, Session 2, Boulder, Colo.
Heinrich, R., Rapoport, T. A. (1974) Eur. J. Biochem. 41: 89-95.
Hugler, M., Menendez, C., Schagger, H., Fuchs, G. (2002) J Bacteriol 184(9): 2404-10.
Ibarra, R. U., Edwards, J. S., Palsson, B. O. (2002) Nature 420(6912): 186-9.
Ignizio, J. P., Cavalier, T. M. 1994. Linear programming. Englewood Cliffs, N.J., Prentice Hall.
Kacser, H., Burns, J. A. (1973). Symp. Soc. Exp. Biol. 27: 65-104.
Kanehisa, M., Goto, S., Kawashima, S., Okuno, Y. & Hattori, M. (2004) Nucleic Acids Res 32 Database issue, D277-80.
Karp, P. D., Riley, M., Saier, M., Paulsen, I. T., Collado-Vides, J., Paley, S. M., Pellegrini-Toole, A., Bonavides, C. & Gama-Castro, S. (2002) Nucleic Acids Res 30, 56-8.
Kataoka, N., Miya, A. & Kiriyama, K. (1997) Wat. Sci. Tech. 36, 41-47.
Kompala, D. S., Ramkrishna, D., Tsao, G. T. (1984) Biotechnol Bioeng 26(11): 1272-1281.
Korotkova, N., Chistoserdova, L. & Lidstrom, M. E. (2002) J Bacteriol 184, 6174-81.
Krieger, C. J., Zhang, P., Mueller, L. A., Wang, A., Paley, S., Arnaud, M., Pick, J., Rhee, S. Y. & Karp, P. D. (2004) Nucleic Acids Res 32 Database issue, D438-42.
Li, K. & Frost, J. W. (1998) Journal of American Chemical Society 120, 10545-10546.
Liu, H., Ramnarayanan, R. & Logan, B. E. (2004) Environmental Science and Technology 38, 2281-2285.
Lovley, D. R. (2003) Nat Rev Microbiol 1, 35-44.
Majewski, R. A., Domach, M. M. (1990) Biotechnol Bioeng 35: 732-738.
Mavrovouniotis, M., Stephanopoulos, G. & Stephanopoulos, G. (1990) Biotechnol Bioeng 36, 1119-1132.
McShan, D. C., Rao, S. & Shah, I. (2003) Bioinformatics 19, 1692-8.
Menendez, C., Bauer, Z., Huber, H., Gad'on, N., Stetter, K. O., Fuchs, G. (1999) J Bacteriol 181(4): 1088-98.
Methe, B. A., Nelson, K. E., Eisen, J. A., Paulsen, I. T., Nelson, W., Heidelberg, J. F., Wu, D., Wu, M., Ward, N., Beanan, M. J., et al. (2003) Science 302, 1967-9.
Misawa, N., Yamano, S. & Ikenaga, H. (1991) Appl Environ Microbiol 57, 1847-9.
Nakamura, C. E. & Whited, G. M. (2003) Curr Opin Biotechnol 14, 454-9.
Nakamura, C. E. 2002. Production of 1,3-Propanediol by E. coli. presented at Metab Eng IV Conf: Tuscany, Italy.
Nandi, R. & Sengupta, S. (1996) Enzyme and microbial tehcnology 19, 20-25.
Nandi, R. & Sengupta, S. (1998) Crit Rev Microbiol 24, 61-84.
Neidhardt, F. C., Curtiss, R. 1996. *Escherichia coli* and *Salmonella*: cellular and molecular biology. Washington, D.C., ASM Press.
Overbeek, R., Larsen, N., Pusch, G. D., D'Souza, M., Selkov, E., Jr., Kyrpides, N., Fonstein, M., Maltsev, N. & Selkov, E. (2000) Nucleic Acids Res 28, 123-5.
Papin, J. A., Price, N. D., Wiback, S. J., Fell, D. A., Palsson, B. 2003. Metabolic Pathways in the Post-Genome Era. Trends Biochem Sci, accepted.
Papoutsakis, E. & Meyer, C. (1985) Biotechnol Bioeng 27, 50-66.
Papoutsakis, E. (1984) Biotechnol Bioeng 26, 174-187.
Pharkya, P., Burgard, A. P. & Maranas, C. D. (2003) Biotechnol Bioeng 84, 887-99.
Price, N. D., Papin, J. A., Schilling, C. H., Palsson, B. 2003. Genome-scale Microbial In Silico Models: The Constraints-Based Approach. Trends Biotechnol, accepted.
Ramakrishna, R., Edwards, J. S., McCulloch, A., Palsson, B. O. (2001) Am J Physiol Regul Integr Comp Physiol 280(3): R695-704.
Ramakrishna, R., Ramakrishna, D., Konopka, A. E. (1996). Biotechnol Bioeng 52: 141-151.
Reed, J. L., Vo, T. D., Schilling, C. H. & Palsson, B. O. (2003) Genome Biol 4, R54.
Schilling, C. H., Covert, M. W., Famili, I., Church, G. M., Edwards, J. S. & Palsson, B. O. (2002) J Bacteriol 184, 4582-93.
Schilling, C. H., Covert, M. W., Famili, I., Church, G. M., Edwards, J. S., Palsson, B. O. (2002) J Bacteriol 184(16): 4582-93.
Schilling, C. H., Palsson, B. O. (2000) J Theor Biol 203(3): 249-83.
Segre, D., Vitkup, D., Church, G. M. (2002) Proc Natl Acad Sci USA 99(23): 15112-7.
Segre, D., Zucker, J., Katz, J., Lin, X., D'Haeseleer, P., Rindone, W. P., Kharchenko, P., Nguyen, D. H., Wright, M. A. & Church, G. M. (2003) Omics 7, 301-16.
Selkov, E., Jr., Grechkin, Y., Mikhailova, N. & Selkov, E. (1998) Nucleic Acids Res 26, 43-5.
Seressiotis, A. & Bailey, J. E. (1988) Biotechnol Bioeng 31, 587-602.

Stephanopoulos, G., Aristidou, A. A., Nielsen, J. 1998. Metabolic engineering: principles and methodologies. San Diego, Academic Press.

Stephanopoulos, G. & Sinskey, A. J. (1993) Trends Biotechnol 11, 392-6.

Stols, L., Donnelly, M. I. (1997) Appl Environ Microbiol 63(7): 2695-701.

Tomita, M., Hashimoto, K., Takahashi, K., Shimizu, T. S., Matsuzaki, Y., Miyoshi, F., Saito, K., Tanida, S., Yugi, K., Venter, J. C., et al. (1999) Bioinformatics 15, 72-84.

Valdes, J., Veloso, F., Jedlicki, E. & Holmes, D. (2003) BMC Genomics 4, 51.

Van Dien, S. J. & Lidstrom, M. E. (2002) Biotechnol Bioeng 78, 296-312.

Van Dien, S. J., Strovas, T. & Lidstrom, M. E. (2003) Biotechnol Bioeng 84, 45-55.

Varma, A., Boesch, B. W., Palsson, B. O. (1993) Appl Environ Microbiol 59(8): 2465-73.

Varma, A, Palsson, B. O. (1993) J. Theor. Biol. 165: 503-522.

Varma, A. & Palsson, B. O. (1994) Bio/Technology 12, 994-998.

Varner, J., Ramkrishna, D. (1999) Biotechnol Prog 15(3): 407-25.

Varner, J. & Ramkrishna, D. (1999) Curr Opin Biotechnol 10, 146-150.

Zeikus, J. G., Jain, M. K., Elankovan, P. (1999) Appl Microbiol Biotechnol 51: 545-552.

Zeng, A. P., Biebl, H. (2002) Adv Biochem Eng Biotechnol 74: 239-59.

Zhu, M. M., Lawman, P. D., Cameron, D. C. (2002) Biotechnol Prog 18(4): 694-9.

What is claimed is:

1. A method for producing a stored representation of a modified metabolic microbial network based on an organism-specific metabolic network with added functionalities to enable a desired biotransformation of a production host, the stored representation comprising a plurality of metabolic pathways which include at least one stoichiometrically balanced pathway, wherein each of the method steps is performed on a suitably programmed computer, said method steps comprising:
    (a) accessing reactions from a universal database to provide stoichiometric balance;
    (b) calculating a maximum theoretical yield of a product associated with a substrate;
    (c) identifying the at least one stoichiometrically balanced pathway based on the reactions, the substrate, and the maximum theoretical yield of the product to minimize a number of non-native functionalities in the production host;
    (d) incorporating the at least one stoichiometrically balanced pathway into the production host to provide the desired biotransformation; and
    (e) providing an output of said modified metabolic microbial network to a user.

2. The method of claim 1 wherein the stored representation is stored in a bioengineered organism.

* * * * *